United States Patent [19]
Feldmann et al.

[11] Patent Number: 5,633,145
[45] Date of Patent: May 27, 1997

[54] TNFα RECEPTOR-DERIVED BINDING PROTEIN

[75] Inventors: Marc Feldmann, Hammersmith, United Kingdom; Patrick W. Gray, Bothell, Wash.; Martin J. C. Turner, Ann Arbor, Mich.; Fionula M. Brennan, Hammersmith, United Kingdom

[73] Assignee: The Mathilda and Terence Kennedy Institute of Rheumatology, London, England

[21] Appl. No.: 50,319

[22] PCT Filed: Oct. 18, 1991

[86] PCT No.: PCT/GB91/01826

§ 371 Date: May 10, 1993

§ 102(e) Date: May 10, 1993

[87] PCT Pub. No.: WO92/07076

PCT Pub. Date: Apr. 30, 1992

[30] Foreign Application Priority Data

Oct. 18, 1990 [GB] United Kingdom .................... 9022648

[51] Int. Cl.$^6$ .............................. C12N 5/10; C12N 15/12
[52] U.S. Cl. .................... 435/69.1; 435/69.7; 435/252.3; 435/37.1; 536/23.4; 536/23.5
[58] Field of Search ................................. 435/69.1, 69.7; 530/350; 536/23.4; 514/2

[56] References Cited

FOREIGN PATENT DOCUMENTS 308378  3/1989  European Pat. Off. .
393438  10/1990  European Pat. Off. .

OTHER PUBLICATIONS

Yan et al., *J. Biol. Chem.* 266(18):12098–12104, Jun. 25, 1991.

Brennan et al., "Inhibitory Effect of TNFα Antibodies on Synovial Cell Interleukin–1 Production in Rheumatoid Arthritis," *Lancet* ii:244–247 (1989).

Haworth et al., "Applications of Cytokines in Human Immunotherapy" in *Immunology and Molecular Biology of Cytokines* (ed. A.W. Thompson) Academic Press, pp. 301–324 (1991).

Williams et al., "Anti–TNF Ameliorates Joint Disease in Murine Collagen–Induced Arthritis," *Proc. Natl. Acad. Sci. USA* 89:9784–9788 (1992).

Elliott et al., "Treatment of Rheumatoid Arthritis with Chimeric Monoclonal Antibodies to TNFα," *Arth. Rheum.* 36:1681–1690 (1993).

Elliott et al., "Randomised Double Blind Comparison of a Chimeric Monoclonal Antibody to Tumour Necrosis Factor α(cA2) versus Placebo in Rheumatoid Arthritis," *Lancet* 344:1105–1110 (1994).

Elliott et al., "Repeated Therapy with Monoclonal Antibody to Tumour Necrosis Factor α(cA2) in Patients with Rheumatoid Arthritis," *Lancet* 344:1125–1127 (1994).

Corcoran et al., "Characterization of Ligand Binding by the Human p55 Tumour–Necrosis–Factor Receptor, Involvement of Individual Cysteine–Rich Repeats," *Eur. J. Biochem.* 223:831–840 (1994).

Rankin et al., "The Therapeutic Effects of an Engineered Human Anti–Tumour Necrosis Factor Alpha Antibody (CDP571) in Rheumatoid Arthritis," *Brit. J. of Rheum.* 34:334–342 (1995).

Butler et al., "Modulation of Proinflammatory Cytokine Release in Rheumatoid Synovial Membrane Cell Cultures with an Anti TNFα Monoclonal: Comparison with Blockade of IL–1 using the Recombinant IL–1 Receptor Antagonist," *European Cytokine Network* (in press).

Schall et al., *Cell* (1990) 61:361–370.

Loetscher et al., *Cell* (1990) 61:351–359.

Gray et al., *Proc. Natl. Acad. Sci. USA* (1990) 87:7380–7384.

*Primary Examiner*—John Ulm
*Attorney, Agent, or Firm*—Reed & Robins

[57] ABSTRACT

A polypeptide is provided which is capable of binding human TNFα and which has the first three cysteine-rich subdomains, but not the fourth cysteine-rich subdomain, of the extracellular binding domain of a receptor selected from the group consisting of the 55 kD and 75 kD receptors for human TNFα. The ability of the polypeptide to bind TNFα means that it can be used for treating diseases mediated by TNFα activity, such as rheumatoid arthritis.

9 Claims, 14 Drawing Sheets

FIG. 1A

```
  1 ACCA GTGATCTCTA TGCCCGAGTC TCAACCCTCA ACTGTCACCC CAAGGCACTT GGGACGTCCT GGACAGACCG
 75 AGTCCCGGGA AGCCCCAGCA CTGCCGCTGC CACACTGCCC TGAGCCCAAA TGGGGGAGTG AGAGGCCATA GCTGTCTGGC

40 Met Gly Leu Ser Thr Val Pro Asp Leu Leu Leu Pro Leu Val Leu Leu Glu Leu Leu Val Gly Ile Tyr Pro
156 ATG GGC CTC TCC ACC GTG CCT GAC CTG CTG CTG CCG CTG GTG CTC CTG GAG CTG TTG GTG GGA ATA TAC CCC

16 Ser Gly Val Ile Gly Leu Val Pro His Leu Gly Asp Arg Glu Lys Arg Asp Ser Val Cys Pro Gln Gly Lys
228 TCA GGG GTT ATT GGA CTG GTC CCT CAC CTA GGG GAC AGA GAG AAG AGA GAT AGT GTG TGT CCC CAA GGA AAA

9 Tyr Ile His Pro Gln Asn Asn Ser Ile Cys Cys Thr Lys Cys His Lys Gly Thr Tyr Leu Tyr Asn Asp Cys
300 TAT ATC CAC CCT CAA AAT AAT TCG ATT TGC TGT ACC AAG TGC CAC AAA GGA ACC TAC TTG TAC AAT GAC TGT

33 Pro Gly Pro Gly Gln Asp Thr Asp Cys Arg Glu Cys Glu Ser Gly Ser Phe Thr Ala Ser Glu Asn His Leu
372 CCA GGC CCG GGG CAG GAT ACG GAC TGC AGG GAG TGT GAG AGC GGC TCC TTC ACC GCT TCA GAA CAC CTC

57 Arg His Cys Leu Ser Cys Ser Lys Cys Arg Lys Glu Met Gly Gln Val Glu Ile Ser Ser Cys Thr Val Asp
444 AGA CAC TGC CTC AGC TGC TCC AAA TGC CGA AAG GAA ATG GGT CAG GTG GAG ATC TCT TGC ACA GTG GAC

81 Arg Asp Thr Val Cys Gly Cys Arg Lys Asn Gln Tyr Arg His Tyr Trp Ser Glu Asn Leu Phe Gln Cys Phe
516 CGG GAC ACC GTG TGT GGC TGC AGG AAG AAC CAG TAC CGG CAT TAT TGG AGT GAG AAC CTT TTC CAG TGC TTC

105 Asn Cys Ser Leu Cys Leu Asn Gly Thr Val His Leu Ser Cys Gln Glu Lys Gln Asn Thr Val Cys Thr Cys
558 AAT TGC AGC CTC TGC CTC AAT GGG ACC GTG CAC CTC TCC TGC CAG GAG AAG CAG AAC ACC GTG TGC ACG

129 His Ala Gly Phe Phe Leu Arg Glu Asn Glu Cys Val Ser Cys Ser Asn Cys Lys Lys Ser Leu Glu Cys Thr
660 CAT GCA GGT TTC TTT CTA AGA GAA AAT GAG TGC GTC TCC TGT AGT AAC TGT AAG AAG AGC CTG GAG TGC ACG

153 Lys Leu Cys Leu Pro Gln Ile Glu Leu Leu Ser Gly Lys Thr Arg Ser Asp Thr Lys Thr Thr Arg Lys Pro Leu
732 AAG TTG TGC CTA CCC CAG ATT GAG CTT TTA TCC GGC GAC ACT AAG ACA CGC ACA CGC CCC CTG

177 Val Ile Phe Gly Leu Leu Phe Gly Leu Met Tyr Arg Val Tyr Gln Trp Lys
804 GTC ATT TTT GGT CTC CTC TTA GGT ATG TAT CGC GTG TAC CAA TGG AAG

201 Ser Lys Leu Tyr Ser Ile Val Cys Gly Lys Ser Thr Pro Glu Lys Glu Gly Glu Leu Glu Gly Thr Thr Thr
876 TCC AAG CTC TAC TCC ATT GTT TGT GGG AAA TCG ACA CCT GAA AAA GAG GGG GAG CTT GAA GGA ACT ACT
```

```
225 Lys Pro Leu Ala Pro Asn Ser Phe Ser Pro Thr Pro Thr Leu Gly Phe Ser Pro Val
948 AAG CCC CTG GCC CCA AAC AGC TTC AGT CCC ACT CCA ACC CTG GGC TTC AGT CCC GTG

249 Pro Ser Ser Thr Phe Pro Pro Tyr Ser Ser Thr Pro Gly Asp Cys Pro Asn Phe Ala Ala Pro Arg
1020 CCC AGT TCC ACC TTC CCA CCA TAT TCC AGC ACC CCC GGT GAC TGT CCC AAC TTT GCG GCT CGC AGA

273 Glu Val Ala Pro Tyr Gln Gly Ala Thr Ile Leu Leu Pro Gly Asp Pro Ala Thr Pro Ile Asn
1092 GAG GTG GCA CCA TAT CAG GGG GCT ACA ATC CTT CTG CCA GGT GAC CCC GCG ACG CCC ATC AAC

297 Pro Leu Gln Lys Trp Glu Asp Ser Ala His Lys Pro Thr Leu Ser Asp Thr Ala Pro Leu Tyr
1164 CCC CTT CAG AAG TGG GAG GAT AGC GCT CAC AAA CCA TTG AGC AGC CTA GAC ACT GCG CTG TAC

321 Ala Val Val Glu Asn Val Pro Leu Gln Leu Phe Arg Val Arg Arg Leu Gly Ala Leu His Glu
1236 GCC GTG GTG GAG AAC GTG CCC CCG CTG CAG CTT TTC CGG GTG GTG AGG CTA GGG GCC CAC GAG

345 Ile Asp Arg Leu Glu Leu Asn Gly Gln Tyr Ser Met Leu Ser Asp Arg
1308 ATC GAT CGG CTG GAG CTG CAG AAC CAA TAC AGC ATG CTA AGC GAC CGC

369 Arg Arg Pro Arg Arg Arg Arg Arg Glu Arg Glu Leu Arg Arg Val Leu Gly Met Ala Leu Leu Gly
1380 CGC CGG CCG CGG CGG CGG CGC CGC GAG CGG GAG CTG CGG AGA CGC GGA GTG CTC CGC GAC CTG GGC

393 Cys Leu Glu Glu Ala Ile Glu Glu Ala Leu Cys Gly Pro Ala Ala Leu Pro Pro Ala Leu Leu Arg
1452 TGC CTG GAG GAG GCC ATC GAG GAG GCG CTT TGC GGC CTC CCG GCC GCC CCA CCG CCG GCC CTC CTC CTC
1521 GGCTGCGCCC TGCGGGCAGC TCTAAGGACC AACCCCACTT TTTTCTGGAA AGGAGGGGTC
1601 CTGCAGGGGC AAGCAGGAGC TAGCAGCAGC GATGTACATA GCTTTTCTCA GCTGCCTGCG
1681 CGCCGGCGAC AGTCAGGCT GTGCGCGGCG CTAACCCCTC CAAGAGCCTG AGTGGGTGGT TTGCGAGGAT
1761 GAGGGACGCT ATGCCTCATG CAGCCTAAGC CCCGTTTTGG AGAGAGGTGC GCTCGGGGGC CCCTGGTTCG TCCCTGAGCC
1841 TTTTCACAG TGCATAAGCA GTTTTTGTTT GTGTCCTCAC TCAATCATGT TACACTAATA
1921 GAAACTTGGC ACTCCTGTGC CCTCTGCCTG GACAAGCAC ATAGCAAGCT GAACTGTCCT AAGGCAGGGG CGAGCACGGA
2001 ACAATGGGGC CTTCAGCTGG AGCTGTGGAC TTTTGTACAT ACACTAAAAT TCTGAAGTTA AG
```

DNA sequence   608 b.p.   TGTCTGGCATGG ... CCCCAGATTTAG   linear

```
    9 /  1                                        39 /  11
  ATG GGC CTC TCC ACC GTG CCT GAC CTG CTG CCG CTG GTG CTG CTG TTG GTG
  met gly leu ser thr val pro asp leu leu pro leu val leu leu leu val
   69 /  21                                        99 /  31
  GGA ATA TAC CCC TCA GGG GTT ATT GGA CTG CCT CAC CTA GGG GAC GAG AAG AGA
  gly ile tyr pro ser gly val ile gly leu pro his leu gly asp arg glu lys arg
  129 /  41                                       159 /  51
  GAT AGT GTG TGT CCC CAA GGA AAA TAT ATC CAC CCT CAA AAT TCG ATT TGC TGT ACC
  asp ser val cys pro gln gly lys tyr ile his pro gln asn ser ile cys cys thr
  189 /  61                                       219 /  71
  AAG TGC CAC AAA GGA ACC TAC TTG TAC AAT GAC TGT CCA GGC CCG GGG CAG GAT ACG GAC
  lys cys his lys gly thr tyr leu tyr asn asp cys pro gly pro gly gln asp thr asp
  249 /  81                                       279 /  91
  TGC AGG GAG AGC GGC TCC TTC ACC GCT TCA GAA AAC CTC AGA CAC TGC CTC
  cys arg glu cys gly ser phe thr ala ser glu asn leu arg his cys leu
  309 / 101                                       339 / 111
  AGC TGC TCC AAA TGC CGA AAG GAA ATG GGT CAG GTG GAG ATC TGC TCT TGC ACA GTG GAC
  ser cys ser lys cys arg lys glu met gly gln val glu ile ser cys thr val asp
  369 / 121                                       399 / 131
  CGG GAC ACC GTG TGT GGC TGC AGG AAG AAC TAC CGG CAT TAT TGG AGT GAA AAC CTT
  arg asp thr val cys gly cys arg lys asn tyr arg his tyr trp ser glu asn leu
  429 / 141                                       459 / 151
  TTC CAG TGC TTC AAT TGC AGC CTC TGC CTC AAT GGG ACC TTC CAC GTG TGC CAG GAG
  phe gln cys phe asn cys ser leu cys leu asn gly thr phe his val cys gln glu
  489 / 161                                       519 / 171
  AAA CAG AAC ACC GTG TGC ACC TGC CAT GCA GGT TTC TTT CTA AGA GAA AAC GAG TGT GTC
  lys gln asn thr val cys thr cys his ala gly phe phe leu arg glu asn glu cys val
  549 / 181                                       579 / 191
  TCC TGT AGT AAC TGT AAG AAA AGC CTG TGC ACG AAG TTG TGC CTA CCC CAG ATT TAG
  ser cys ser asn cys lys lys ser leu cys thr lys leu cys leu pro gln ile AMB
```

FIG. 7

```
DNA sequence   482 b.p.   TGTCTGGCATGG ... CCCCAGATTTAG   linear 1                                              39 /           11
ATG GGC CTC TCC ACC GTG CCT GAC CTG CTG GTG CTC CTG GAG CTG TTG GTG
met gly leu ser thr val pro asp leu leu val leu leu glu leu leu val
 69 /           21                              99 /           31
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
129 /           41                             159 /           51
GAG TGT GAG AGC GGC TCC TTC ACC GCT TCA GAA AAC CAC CTC AGA CAC TGC CTC AGC TGC
glu cys glu ser gly ser phe thr ala ser glu asn his leu arg his cys leu ser cys
189 /           61                             219 /           71
TCC AAA TGC CGA AAG GAA ATG GGT CAG GTG GAG ATC TCT TGC ACA GTG GAC CGG GAC
ser lys cys arg lys glu met gly gln val glu ile ser cys thr val asp arg asp
249 /           81                             279 /           91
ACC GTG TGT GGC TGC AGG AAG AAC CAG TAC CGG CAT TAT TGG AGT GAA AAC CTT TTC CAG
thr val cys gly cys arg lys asn gln tyr arg his tyr trp ser glu asn leu phe gln
309 /          101                             339 /          111
TGC TTC AAT TGC AGC CTC TGC CTC AAT GGG ACC GTG CAC CTC TCC TGC CAG GAG AAA CAG
cys phe asn cys ser leu cys leu asn gly thr val his leu ser cys gln glu lys gln
369 /          121                             399 /          131
AAC ACC GTG TGC ACC TGC CAT GCA GGT TTC TTT CTA AGA GAA AAC GAG TGT GTC TCC TGT
asn thr val cys thr cys his ala gly phe phe leu arg glu asn glu cys val ser cys
429 /          141                             459 /          151
AGT AAC TGT AAG AAA AGC CTG GAG TGC ACG AAG TTG TGC CTA CCC CAG ATT TAG
ser asn cys lys lys ser leu glu cys thr lys leu cys leu pro gln ile AMB
```

FIG. 8

```
DNA  sequence    470 b.p.    TGTCTGGCATGG ... CCCCAGATTTAG   linear

9 /  1                       39 /  11
  ATG GGC CTC TCC ACC GTG CCT GAC CTG CTG CCG CTG CTC GTG CTG GAG CTG TTG GTG
  met gly leu ser thr val pro asp leu leu pro leu leu val leu leu glu leu leu val
   69 /  21                      99 /  31
  GGA ATA TAC CCC TCA GGG GTT ATT GGA CTG GTC CCT CAC CTA GGG GAC AGG GAG AAG AGA
  gly ile tyr pro ser gly val ile gly leu val pro his leu gly asp arg glu lys arg
  129 /  41                     159 /  51
  GAT AGT GTG TGT CCC CAA GGA AAA TAT ATC TAC ATC CAC CCT CAA AAT AAT TCG ATT TGC TGT ACC
  asp ser val cys pro gln gly lys tyr ile tyr ile his pro gln asn asn ser ile cys cys thr
  189 /  61                     219 /  71
  AAG TGC CAC AAA GGA ACC TAC TTG TAC AAT GAC TGT CCA GGC CCG GGG CAG GAT ACG GAC
  lys cys his lys gly thr tyr leu tyr asn asp cys pro gly pro gly gln asp thr asp
  249 /  81                     279 /  91
  TGC AGG AAG AAC CAG TAC CGG CAT TAT GGG ACC GTG CTT TTC CAG TGC TTC AAT TGC
  cys arg lys asn gln tyr arg his tyr trp ser glu asn leu phe gln cys phe asn cys
  309 / 101                     339 / 111
  AGC CTC TGC CTC AAT GGG ACC CTC CAC GTG CAC CTC TGC CAG GAG AAA CAG AAC ACC GTG TGC
  ser leu cys leu asn gly thr val his val his leu cys gln glu lys gln asn thr val cys
  369 / 121                     399 / 131
  ACC TGC CAT GCA GGT TTC TTT CTA AGA GAA AAC GAG TGT GTC TCC TGT AGT AAC TGT AAG
  thr cys his ala gly phe phe leu arg glu asn glu cys val ser cys ser asn cys lys
  429 / 141                     459 / 151
  AAA AGC CTG GAG TGC ACG AAG TTG TGC CTA CCC CAG ATT TAG
  lys ser leu glu cys thr lys leu cys leu pro gln ile AMB

FIG. 9
```

```
DNA sequence    485 b.p.    TGTCTGGCATGG ... CCCCAGATTTAG    linear

9 /    1
ATG GGC CTC TCC ACC GTG CCT GAC CTG CTG CCG CTG GTG CTC CTG GAG CTG CTC TTG GTG
met gly leu ser thr val pro asp leu leu pro leu val leu leu glu leu leu leu val
 69 /   21                              39 /   11
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
129 /   41                              99 /   31
GAT AGT GTG TGT CCC CAA GGA ACC TAC ATC AAA TAT ATC CAC CCT CAA AAT TCG ATT TGC TGT ACC
asp ser val cys pro gln gly thr tyr ile lys tyr ile his pro gln asn ser ile cys cys thr
189 /   61                             159 /   51
AAG TGC CAC AAA GGA ACC TAC TTG TAC TTG TAC AAT GAC TGT CCA GGC CCG GGG CAG GAT ACG GAC
lys cys his lys gly thr tyr leu tyr leu tyr asn asp cys pro gly pro gly gln asp thr asp
249 /   81                             219 /   71
TGC AGG GAG TGT GAG AGC GGC TCC TTC ACC GCT TCA GAA AAC CAC CTC AGA CAC TGC CTC
cys arg glu cys glu ser gly ser phe thr ala ser glu asn his leu arg his cys leu
309 /  101                             279 /   91
AGC TGC TCC AAA TGC CGA AAG GAA ATG GGT CAG GTG CAG GTG GAG ATC TCT TGC ACA GTG GAC
ser cys ser lys cys arg lys glu met gly gln val gln val glu ile ser cys thr val asp
369 /  121                             339 /  111
CGG GAC ACC GTG TGT ACC TGC CAT GCA GGT TTC TTT CTA AGA GAA AAC GAG TGT GTC TCC
arg asp thr val cys thr cys his ala gly phe phe leu arg glu asn glu cys val ser
429 /  141                             399 /  131
TGT AGT AAC TGT AAG AAA AGC CTG GAG TGC ACG AAG TTG TGC CTA CCC CAG ATT TAG
cys ser asn cys lys lys ser leu glu cys thr lys leu cys leu pro gln ile AMB
                                       459 /  151
```

FIG. 10

```
DNA sequence  512 b.p.  TGTCTGGCATGG ... GTGTGCACCTGA  linear 1                                     11
  9 /
ATG GGC CTC TCC ACC GTG CCT GAC CTG CTG CCG CTG GTG CTC CTG GAG CTG TTG GTG
met gly leu ser thr val pro asp leu leu pro leu val leu leu glu leu leu val
 69 /                              21                                     31
GGA ATA TAC CCC TCA GGG GTT ATT GGA CTG GTC CCT CAC CTA GGG GAC AGG GAG AAG AGA
gly ile tyr pro ser gly val ile gly leu val pro his leu gly asp arg glu lys arg
129 /                              41                                     51
GAT AGT GTG TGT CCC CAA GGA AAA TAT ATC CAC CCT CAA AAT AAT TCG ATT TGC TGT ACC
asp ser val cys pro gln gly lys tyr ile his pro gln asn asn ser ile cys cys thr
189 /                              61                                     71
AAG TGC CAC AAA GGA ACC TAC TTG TAC AAT GAC TGT CCA GGC CAG CCG GGG CAG GAT ACG GAC
lys cys his lys gly thr tyr leu tyr asn asp cys pro gly gln pro gly gln asp thr asp
249 /                              81                                     91
TGC AGG GAG TGT GAG AGC GGC TCC TTC ACC GCT TCA GAA GGT GGT CAG ATC TCT TGC ACA GTG GAC
cys arg glu cys glu ser gly ser phe thr ala ser glu val gly gln ile ser ser cys thr val asp
309 /                             101                                    111
AGC TGC TCC AAA TGC CGA AAG GAA ATG GGT CAG GTG CAG AAC TAC CGG CAT TAT TGG AGT GAA AAC CTT
ser cys ser lys cys arg lys glu met gly gln val gln asn tyr arg his tyr trp ser glu asn leu
369 /                             121                                    131
CGG GAC ACC GTG TGT GGC TGT AAG AAC AAC CAG CAG TAC CGG CAT TAT TGG AGT GAA AAC CTT
arg asp thr val cys gly cys arg lys asn asn gln gln tyr arg his tyr trp ser glu asn leu
429 /                             141                                    151
TTC CAG TGC TTC AAT TGC AGC CTC TGC CTC AAT GGG ACC GTG CAC CTC TCC TGC CAG GAG
phe gln cys phe asn cys ser leu cys leu asn gly thr val his leu ser cys gln glu
489 /                             161
AAA CAG AAC ACC GTG TGC ACC TGA
lys gln asn thr val cys thr OPA
```

FIG. 11

TNFα RECEPTOR-DERIVED BINDING PROTEIN

The present invention relates to recombinant proteins and their use.

Tumour necrosis factor-α (TNFα) is a potent cytokine which elicits a broad spectrum of biological responses. TNFα causes the cytolysis or cytostasis of many tumour cell lines in vitro, induces the haemorrhagic necrosis of transplanted tumours in mice, enhances the phagocytosis and cytotoxicity of polymorphonuclear neutrophils, and modulates the expression of many proteins, including lipoprotein lipase, class I antigens of the major histo-compatibility complex, and cytokines such as interleukin 1 and interleukin 6. TNFα appears to be necessary for a normal immune response, but large quantities produce dramatic pathogenic effects. TNFα has been termed "cachectin" since it is the predominant factor responsible for the wasting syndrome (cachexia) associated with neoplastic disease and parasitemia. TNF is also a major contributor to toxicity in gram-negative sepsis, since antibodies against TNF can protect infected animals.

The many activities of TNFα are mediated by binding to a cell surface receptor. Radioligand binding studies have confirmed the presence of TNF receptors on a wide variety of cell types. Although these receptors are expressed in limited numbers (1,000–10,000 receptors/cell), they bind TNFα with high affinity ($K_a=10^9 M^{-1}$ at 4° C.). Lymphotoxin (LT, also termed TNFβ) has similar, if not identical, biological activities to TNFα, presumably because both are recognized by the same receptor.

Recently, several laboratories have detected heterogeneity in TNF receptor preparations. Two distinct cell surface receptors which bind TNFα and TNFβ have recently been characterised at the molecular level. cDNA for one form of the receptor with a Mr of 55 kD was isolated utilising probes designed from the peptide sequence of a soluble form of the receptor (1,2). A second receptor of Mr 75 kD was cloned by a COS cell expression approach (3). Both receptors are members of a larger family of cytokine receptors which include the nerve growth factor receptor, the B cell antigen CD40, the rat T cell antigen MRC OX40. In addition these receptors are homologous to the predicted product of a transcriptionally active open reading frame from shope fibroma virus which appears to give rise to a secreted protein.

The most conserved feature amongst this group of cell surface receptors is the cysteine rich extracellular ligand binding domain, which can be divided into four repeating motifs of about forty amino acids. We have now generated four soluble receptor derivatives of the 55 kD TNFα receptor (TNFR). Each derivative is composed of the extracellular binding domain but without one of the cysteine rich subdomains. We have found that the derivative which lacks the membrane-proximal fourth subdomain retains the ability to bind TNFα with high affinity. This finding has general applicability.

Accordingly, the present invention provides a polypeptide which is capable of binding human TNFα and which consists essentially of:

(a) the first three cysteine-rich subdomains, but not the fourth cysteine-rich subdomain, of the extracellular binding domain of the 55 kD or 75 kD receptor for human TNFα; or (b) an amino acid sequence having a homology of 90% or more with the said sequence (a).

The invention also provides:

a DNA sequence which encodes such a polypeptide;

a vector which incorporates a DNA sequence of the invention and which is capable, when provided in a transformed host, of expressing the polypeptide of the invention encoded by the DNA sequence; and a host transformed with such a vector.

In the accompanying drawings:

FIG. 1 shows the nucleotide sequence of the human TNFα cDNA (SEQ ID NO: 24) and encoded amino acid (SEQ ID NO: 25) sequence. The predicted signal sequence residues are numbered −40 to −1. The transmembrane domain is boxed and potential N-linked glycosylation sites are overlined. The sequence homologous with the designed oligonucleotide probe is found at nucleotide positions 477–533.

FIG. 2 is a Northern blot (lanes 1–3) of 10 μg of oligo-dT selected RNA from human 293 cells (fibroblast cell line) (lane 1), placenta (lane 2) and spleen (lane 3) hybridised with the TNF receptor cDNA (SmaI-EcoRI fragment). The Southern blot (lanes 4–6) was hybridized with the same probe. Human genomic DNA (5 μg per lane) was digested with PstI (lane 4), Hind III (lane 5) and EcoRI (lane 6).

FIG. 3 shows the binding characteristics of recombinant human TNF receptor expressed in COS-7 cells. The direct binding of recombinant $^{125}$I-TNFα to COS-7 cells transfected with prTNFR is presented in panel A. The inset contains Scatchard analysis derived from this data. As shown in panel B, monolayers of Cos-7 cells transfected with TNFR cDNA were incubated with 1 nM $^{125}$I-TNF in the presence of various concentrations of unlabelled TNFα or TNFβ.

FIG. 4 shows the effects of soluble TNFR on TNFα binding and biological activity. Panel A shows the effects of supernatants from Cos-7 cells transfected with a cDNA encoding a soluble form of the TNF receptor (pTNFRecd, closed circles) or mock transfected (open circles) on $^{125}$I-TNF binding to U937 cells. Panel B shows the effects of these supernatants on TNF mediated killing of WEHI 164 (clone 13) line. Assays were performed as described in Materials and Methods.

FIG. 6 shows lined up the amino acid sequences of the four cysteine-rich subdomains of the 55 kD (TNFR-55) and 75 kD (TNFR-75) receptors and of rat nerve growth factor receptor (NGFR), human CD40 and rat OX40. Homology is shown by means of boxes.

FIGS. 7 to 11 show the nucleotide sequence and the predicted amino acid sequence of the encoded polypeptide of pTNFRecd, pΔI, pΔII, pΔIII and pΔIV.

Figure 2:
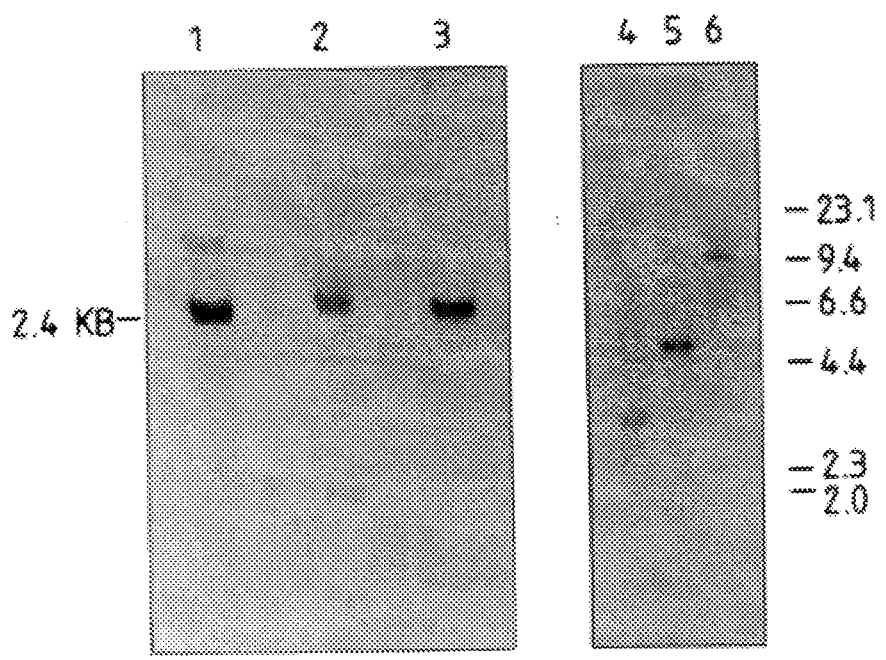

A polypeptide according to the invention is capable of binding human TNFα. Typically the polypeptide has a binding affinity for human TNFα of $10^7 M^{-1}$ or greater, for example $10^8 M^{-1}$ or greater. The affinity may be from $10^7$ to $10^{10} M^{-1}$, for example from $10^8$ to $10^9 M^{-1}$.

A preferred polypeptide consists essentially of the first three cysteine-rich subdomains of the extracellular binding domain of the 55 kD receptor for human TNFα. The sequence (a₁) of these three subdomains is: V C P Q G K Y I H P Q N N S I C C T K C H K G T Y L Y N D C P G P G Q D T D C R E C E S G S F T A S E N H L R H C L S C S K C R K E M G Q V E I S S C T V D R D T V C G C R K N Q Y R H Y W S E N L F Q C F N C S L C L N G T V H L S C Q E K Q N T V C (SEQ ID NO: 4).

A useful polypeptide has the amino acid sequence (c): M G L S T V P D L L L P L V L L E L L V G I Y P S G V I G L V P H L G D R E K R D S V C P Q G K Y I H P Q N N S I C C T K C H K G T Y L Y N D C P G P G Q D T D C R E C E S G S F T A S E N H L R H C L S C S K C R K E M G Q V E I S S C T V D R D T V C G C R K N Q Y R H Y W S E N L F Q C F N C S L C L N G T V H L S C Q E K Q N T V C T (SEQ ID NO: 2).

In an alternative embodiment, the polypeptide may consist essentially of the first three cysteine-rich subdomains of the extracellular binding domain of the 75 kD receptor.

Apart from the amino acid sequence (a), the polypeptides may alternatively consist essentially of an amino acid sequence (b) having a homology of 90% or more with sequence (a). The degree of homology may be 95% or more or 98% or more. Amino acid sequence (a) may therefore be modified by one or more amino acid substitutions, insertions and/or deletions and/or by an extension at either or each end. There should be no modification of the cysteine-residues, however. A polypeptide comprising sequence (b) must of course still be capable of binding human TNFα.

For example, one or more amino acid residues of the sequence (a), other than a cysteine residue, may be substituted or deleted or one or more additional amino acid residues may be inserted; provided the physicochemical character of the original sequence is preserved, i.e. in terms of charge density, hydrophobicity/hydrophilicity, size and configuration. Conservative substitutions may be made. Candidate substitutions are, based on the one-letter code (Eur. J. Biochem. 138, 9–37, 1984):

A for G and vice versa,

V by A, L or G;

K by R;

S by T and vice versa;

E for D and vice versa; and

Q by N and vice versa.

Up to 15 residues may be deleted from the N-terminal and/or C-terminal of the polypeptide, for example up to 11 residues or up to 5 residues.

The polypeptides of the invention consist essentially of sequence (a) or (b). They do not contain a fourth cysteine-rich subdomain. However, the polypeptides may be longer polypeptides of which sequence (a) or (b) is a part. A short sequence of up to 50 amino acid residues may be provided at either or each terminal of sequence (a) or (b). The sequence may have up to 30, for example up to 20 or up to 10, amino acid residues.

Alternatively, a much longer extension may be present at either or each terminal of sequence (a) or (b) of up to, for example, 100 or 200 amino acid residues. Longer amino acid sequences may be fused to either or each end. A chimaeric protein may be provided in which the or each extension is a heterologous amino acid sequence, i.e. a sequence not naturally linked to the amino acid sequence above. Such a chimaeric protein may therefore combine the ability to bind specifically to human TNFα with another functionality.

The polypeptides of the invention lack the fourth cysteine-rich subdomain of the 55 kD or 75 kD receptor as the case may be. In particular, they lack the cysteine residues of the fourth subdomain. They therefore do not comprise, immediately after the third cysteine-rich subdomain, any of the amino acid sequence up to the last cysteine residue of the fourth cysteine-rich subdomain of the relevant receptor except possibly the first amino acid residue of that sequence. The polypeptides may extend beyond that first amino acid residue as indicated above, though, by way of other amino acid sequences.

The polypeptides are typically recombinant polypeptides, although they may be made by synthetic methods such as solid-phase or solution-phase polypeptide synthesis in which case an automated peptide synthesiser may be employed. They may therefore commence with a N-terminal residue M. They are prepared by recombinant DNA technology. The preparation of the polypeptides therefore depends upon the provision of a DNA sequence encoding the polypeptide. A suitable sequence encoding the first three cysteine-rich subdomains of the extracellular binding domain of the 55 kD receptor comprises: GTG TGT CCC CAA GGA AAA TAT ATC CAC CCT CAA AAT AAT TCG ATT TGC TGT ACC AAG TGC CAC AAA GGA ACC TAC TTG TAC AAT GAC TGT CCA GGC CCG GGG CAG GAT ACG GAC TGC AGG GAG TGT GAG AGC GGC TCC TTC ACC GCT TCA GAA AAC CAC CTC AGA CAC TGC CTC AGC TGC TCC AAA TGC CGA AAG GAA ATG GGT CAG GTG GAG ATC TCT TCT TGC ACA GTG GAC CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC AAT GGG ACC GTG CAC CTC TCC TGC CAG GAG AAA CAG AAC ACC GTG TGC (SEQ ID NO: 3).

A DNA sequence may further comprise a DNA sequence encoding a signal sequence fused to the 5' end of the coding sequence. Any signal sequence may be appropriate. The signal sequence should be capable of directing secretion of the polypeptide of the invention from the cell in which the polypeptide is expressed. The signal sequence may be the natural signal sequence for the 55 kD TNFα receptor. An appropriate DNA sequence encoding the first three cysteine-rich subdomains of the extracellular binding domain of the 55 kD receptor and such a signal sequence is therefore: ATG GGC CTC TCC ACC GTG CCT GAC CTG CTG CTG CCG CTG GTG CTC CTG GAG CTG TTG GTG GGA ATA TAC CCC TCA GGG GTT ATT GGA CTG GTC CCT CAC CTA GGG GAC AGG GAG AAG AGA GAT AGT GTG TGT CCC CAA GGA AAA TAT ATC CAC CCT CAA AAT AAT TCG ATT TGC TGT ACC AAG TGC CAC AAA GGA ACC TAC TTG TAC AAT GAC TGT CCA GGC CCG GGG CAG GAT ACG GAC TGC AGG GAG TGT GAG AGC GGC TCC TTC ACC GCT TCA GAA AAC CAC CTC AGA CAC TGC CTC AGC TGC TCC AAA TGC CGA AAG GAA ATG GGT CAG GTG GAG ATC TCT TCT TGC ACA GTG GAC CGG GAC ACC GTG TGT GGC TGC AGG AAG AAC CAG TAC CGG CAT TAT TGG AGT GAA AAC CTT TTC CAG TGC TTC AAT TGC AGC CTC TGC CTC AAT GGG ACC GTG CAC CTC TCC TGC CAG GAG AAA CAG AAC ACC GTG TGC ACC (SEQ ID NO: 1).

A DNA sequence encoding a polypeptide of the invention may be synthesised. Alternatively, it may be constructed by isolating a DNA sequence encoding the 55 kD or 75 kD receptor from a gene library and deleting DNA downstream of the coding sequence for the first three cysteine-rich subdomains of the extracellular binding domain of the receptor. This gives DNA encoding the first three subdomains of either receptor. As an intermediate step, DNA encoding the entire or nearly the entire extracellular binding domain may be isolated and digested to remove DNA downstream of the coding sequence for the first three subdomains.

A modified nucleotide sequence, for example encoding an amino acid sequence (b), may be obtained by use of any appropriate technique, including restriction with an endonuclease, insertion of linkers, use of an exonuclease and/or a polymerase and site-directed mutagenesis. Whether a modified DNA sequence encodes a polypeptide of the invention can be readily ascertained. The polypeptide encoded by the sequence can be expressed in a suitable host and tested for its ability to bind specifically human TNFα.

For expression of a polypeptide of the invention, an expression vector is constructed. An expression vector is prepared which comprises a DNA sequence encoding a polypeptide of the invention and which is capable of expressing the polypeptide when provided in a suitable host. Appropriate transcriptional and translational control elements are provided, including a promoter for the DNA sequence, a transcriptional termination site, and translational start and stop codons. The DNA sequence is provided in the correct frame such as to enable expression of the polypeptide to occur in a host compatible with the vector.

The expression vector is then provided in an appropriate host. Cells harbouring the vector are grown so as to enable expression to occur. The vector may be a plasmid or a viral vector. Any appropriate host-vector system may be employed.

The transformed host may be a prokaryotic or eukaryotic host. A bacterial or yeast host may be employed, for example E. coli or S. cerevisiae. Insect cells can alternatively be used, in which case a baculovirus expression system may be appropriate. As a further alternative, cells of a mammalian cell line, such as Chinese Hamster Ovary (CHO) Cells may be transformed. A polypeptide glycosylated at one, two or three of the sites shown in FIG. 1 can be obtained by suitable choice of the host cell culture.

The polypeptide of the invention can be isolated and purified. The N-terminal of the polypeptide may be heterogeneous due to processing of the translation product within a cell or as the product is being secreted from a cell. A mixture of polypeptides according to the invention, having different N-terminii, may therefore be obtained. The polypeptide is soluble.

The polypeptides of the invention have activity binding human TNFα. This activity is indictive of the possible use of the polypeptides in the regulation of TNFα-mediated responses by binding and sequestering human TNFα, for example possible use in treatment of pulmonary diseases, septic shock, HIV infection, malaria, viral meningitis, graft versus host reactions and autoimmune diseases such as rheumatoid arthritis.

For this purpose, a polypeptide of the present invention may be formulated in a pharmaceutical composition. The pharmaceutical composition also comprises a pharmaceutically acceptable carrier or diluent.

The polypeptide of the invention may be administered to a patient by any convenient route. The choice of whether an oral route or a parenteral route, such as subcutaneous, intravenous or intramuscular administration, is adopted; of the dose; and of the frequency of administration depends upon a variety of factors. These factors include the purpose of the administration, the age and weight of the patient being treated and the condition of the patient. Typically, however, the polypeptide is administered in an amount of from 1 to 1000 μg per dose, more preferably from 10 to 100 μg per dose, for each route of administration.

The following Examples illustrate the invention. A Reference Example is provided.

REFERENCE EXAMPLE

1. Materials and Methods Reagents

Recombinant human TNFα and TNFβ were supplied as highly purified proteins derived from E. coli. The specific activities of these preparations were approximately $10^7$ units/mg, as measured in the murine L929 cell cytotoxicity assay (4). The synthetic oligonucleotides were prepared by Oswel DNA Service (University of Edinburgh).

Isolation of TNFα 55 kD receptor cDNA clones

The sequence of a peptide fragment (E M G Q V E I S S T V D R D T V C G) (SEQ ID NO: 5) of the TNF binding protein was used to design a synthetic oligonucleotide probe (5' AAG GAG ATG GGC CAG GTT GAG ATC TCT TCT ACT GTT GAC AAT GAC ACT GTG TGT GGC-3' (SEQ ID NO: 6)). The 57-mer DNA probe was labelled with $^{32}$P and T4 polynucleotide kinase (New England Biolab, Beverly, Mass.) and used to screen a placenta cDNA library in gt10 (5,6). Approximately 800,000 phage were transferred to nitrocellulose filters and screened at reduced stringency (7). Filters were incubated for 2 hours at 42° C. in 0.05M sodium phosphate, pH 6.5, 20% formamide, 0.75M sodium chloride, 0.075M sodium citrate, 1% polyvinyl pyrrolidone (Sigma, St Louis, Mo.), 1% Ficoll, 1% bovine serum albumin (Sigma), and 50 ng/ml sonicated salmon sperm DNA (Sigma). The radiolabelled probe was then added to the filters ($10^8$ cpm/ml final concentration) which were hybridized for 16 hours. Filters were washed extensively in 0.06M sodium chloride, 0.006M sodium citrate, 1% SDS at 37° C. and positive clones were identified by autoradiography. Ten hybridizing clones were plaque purified (5) and cDNA insert size was determined by polyacrylamide gel electrophoresis of EcoRI digested phage DNA. The inserts of two cDNA clones were sequenced using the dideoxy chain termination technique (8).

Southern and Northern blot analysis

DNA was isolated from human lymphocytes by the method of Blin and Stafford (9) and used for Southern blot analysis (10). DNA was digested with restriction endonucleases (New England Biolabs), fractionated on a 1% agarose gel, and transferred to nitrocellulose. Hybridization and washing were conducted under stringent conditions (6) using a $^{32}$p-labelled preparation of a 600 bp fragment of the TNF receptor cDNA. Northern blot analysis was performed (11) on oligo-dT selected RNA isolated from human placenta, spleen (generously provided by the Cooperative Human Tissue Network, Birmingham, Ala.) and a fibroblast cell line (293 cells). Following electrophoresis on a formaldehyde 1.2% agarose gel, the RNA was transferred to nitrocellulose and hybridized with the TNFα receptor DNA probe under stringent conditions.

Mammalian cell expression of the human TNFα 55 kD receptor and derivatives

The coding region of the majority of the human TNFα 55 kD receptor was isolated as an EcoRI fragment and cloned into a mammalian cell expression vector (12), resulting in plasmid prTNFR. The EcoRI fragment encodes 374 amino acids of the TNF receptor; the 81 carboxyl terminal residues of the cytoplasmic domain are therefore missing from this plasmid construction. A derivative of the TNFα receptor was produced by engineering a termination codon just prior to the transmembrane domain. The polymerase chain reaction (PCR) technique (13) was used to generate a 300 bp restriction fragment containing a BgIII site at the 5' end and a HindIII site preceded by a TAG stop codon at the 3' end. The PCR primers were 5'GCTGCTCCAAATGCCGAAAG (SEQ ID NO: 7)and 5'AGTTCAAGCTTTTACAGTGC-CCTTAACATTCTAA (SEQ ID NO: 8).

The PCR product was gel purified and cloned into the TNF receptor expression plasmid (described above) digested with BgIII and HindIII. DNA sequencing confirmed that the resulting plasmid (pTNFRecd) contained the designed DNA sequence. *E. coli* harbouring pTNFRecd were deposited at the National Collection of Industrial and Marine Bacteria, Aberdeen, GB on 11 Sep. 1990 under accession number NCIMB 40315.

The TNFα receptor expression plasmids were transfected into monkey COS-7 cells using Lipofectin (Gibco BRL, Bethesda, Md.) according to the manufacturer's instructions. Cells were cultured in Dulbecco's modified Eagle's medium containing 10% fetal calf serum.

Analysis of recombinant TNFα 55 kD receptor derivatives

TNFα was radioiodinated with the Iodogen method (Pierce) according to the manufacturer's directions. The specific activity of the $^{125}$I-TNFα was 10–30 µCu/µg. COS cells transfected with the TNFα receptor cDNA (prTNFR, 1300 bp EcoRI fragment) were incubated for 24 hours and then seeded into six well tissue culture plates (Nunc) at $4.5 \times 10^8$ cells per well. The cells were incubated for a further 48 hours and then receptor expression was quantitated by radioligand binding for 2 hours at 4° C. Non-specific binding of $^{125}$I-TNFα was determined in the presence of a 1,000 fold molar excess of unlabelled TNFα. Binding data was analysed by the method of Scatchard (14).

The TNFα receptor derivative was analysed for inhibition of $^{125}$I-TNFα binding to the natural receptor on human U937 cells. Culture supernatant was harvested 72 hours after COS cells were transfected with pTNFRecd. U937 cells ($2 \times 10^8$ cells in 200 µl) were incubated with 1nM $^{125}$I-TNFα and dilutions of COS cell media for 2 hours at 4° C. Cells were then centrifuged through 20% sucrose to remove unbound TNFα. Non-specific binding was determined in the presence of 1 µM unlabelled TNFα.

The TNFα receptor derivative was also analyzed for inhibition of TNFα cytotoxic effects in vitro. The cytotoxicity assay was performed as described on the TNF sensitive cell line WEHI 164 clone 13 (15). Serial dilutions of supernatants from COS cells transfected with pTNFRecd or mock transfected controls were incubated with a constant amount of TNFα (1 ng/ml) for 1 hour at 27° C. before addition to the assay.

2. RESULTS

Isolation and characterization of the TNFα 55 kD receptor cDNA

Figures 1, 3A:
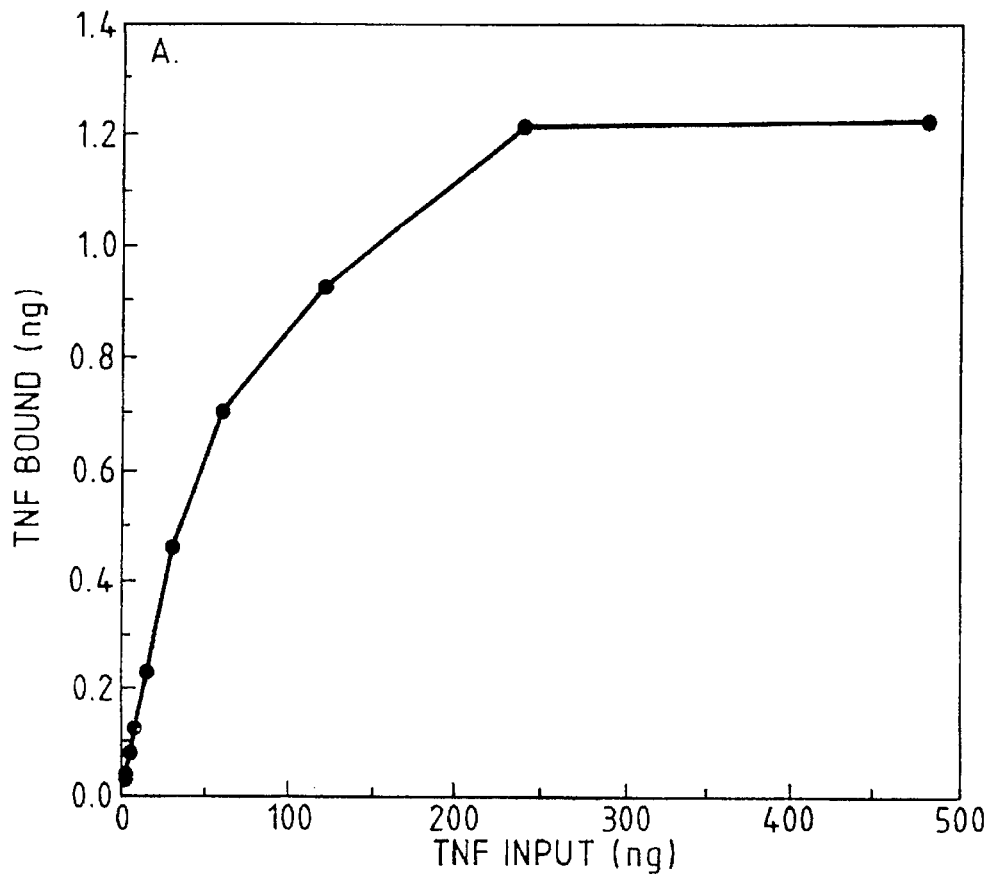

A partial amino acid sequence of the TNF binding protein was used to design a synthetic oligonucleotide probe. The radiolabelled probe was used to screen a human placenta cDNA library in lambdagt10 and ten hybridizing phage were isolated. The nucleotide and deduced amino acid sequences of the longest cDNA clone are depicted in FIG. 1. The third potential ATG initiation codon occurs at position 156 of the nucleotide sequence; the first two ATG codons are closely followed by termination codons, and the third ATG is preceded by the best translation initiation consensus nucleotides (16). The cDNA encodes an open reading frame of 1365 bases which codes for a polypeptide of 455 residues. Both of the peptide sequences determined by amino acid sequencing were identified in the encoded cDNA (17 of 19 and 18 of 19 matching residues). The amino terminal end identified for the TNF binding protein corresponds to the cDNA encoded sequence beginning at residue 41. The first 35 amino acids are generally quite hydrophobic and probably represent a signal sequence. Residues 35–40 are highly charged (DREKR SEQ ID NO: 7)) and such a sequence is not typically found in secretory signal sequences (17); perhaps the natural receptor is processed by proteolysis after residue 40 which contains a dibasio cleavage site (KR). Hydropathy analysis of the protein sequence predicts a single transmembrane domain of 23 amino acids. This hydrophobic sequence divides the protein into an extracellular domain of 171 residues and a cytoplasmic domain of 221 residues. The amino acid composition determined for the TNF binding protein corresponds well with the predicted composition of the extracellular domain encoded by the cDNA (results not shown). The discrepancy between the predicted receptor size (40,000 daltons) and the size determined by SDS-polyacrylamide gel electrophoresis (65,000 daltons, 18–20) is probably due to glycosylation; there are four potential N-linked glycosylation sites in the sequence, three of which are in the extracellular domain. The sequence contains a large number (17) of cysteine residues, 24 of which are in the extracellular domain. The arrangement of these cysteine residues is similar to that of several other cell surface proteins, suggesting that the TNF receptor is structurally related to a family of receptors.

A Northern blot analysis is presented in FIG. 2. The $^{32}$P-labelled cDNA hybridized to a single predominant band of oligo-dT selected RNA from human placenta or spleen. A minor larger transcript was also observed in RNA from a fibroblast cell line. The size of the hybridizing species is 2400 bases, in good agreement with the size of isolated cDNA. Also shown in FIG. 2 is a Southern blot of human genomic DNA hybridized with a 600 bp probe from the cDNA. In each of the three different restriction digests, only a single hybridized signal was observed. Thus the TNF receptor that we have isolated appears to be encoded by a single gene.

Expression of recombinant TNF receptor sequences in mammalian cells

Figures 2, 3A:
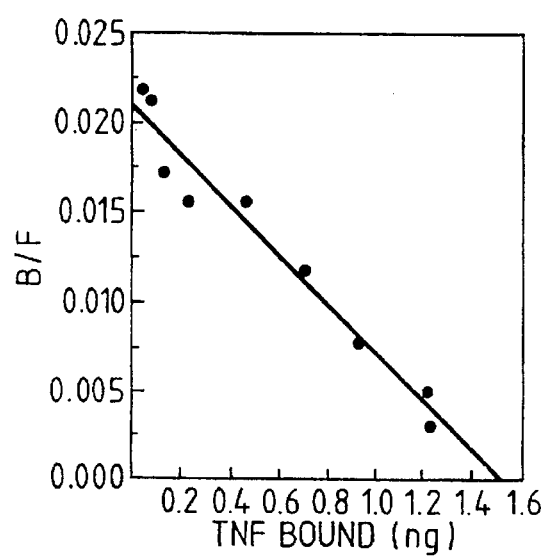
Figure 3B:
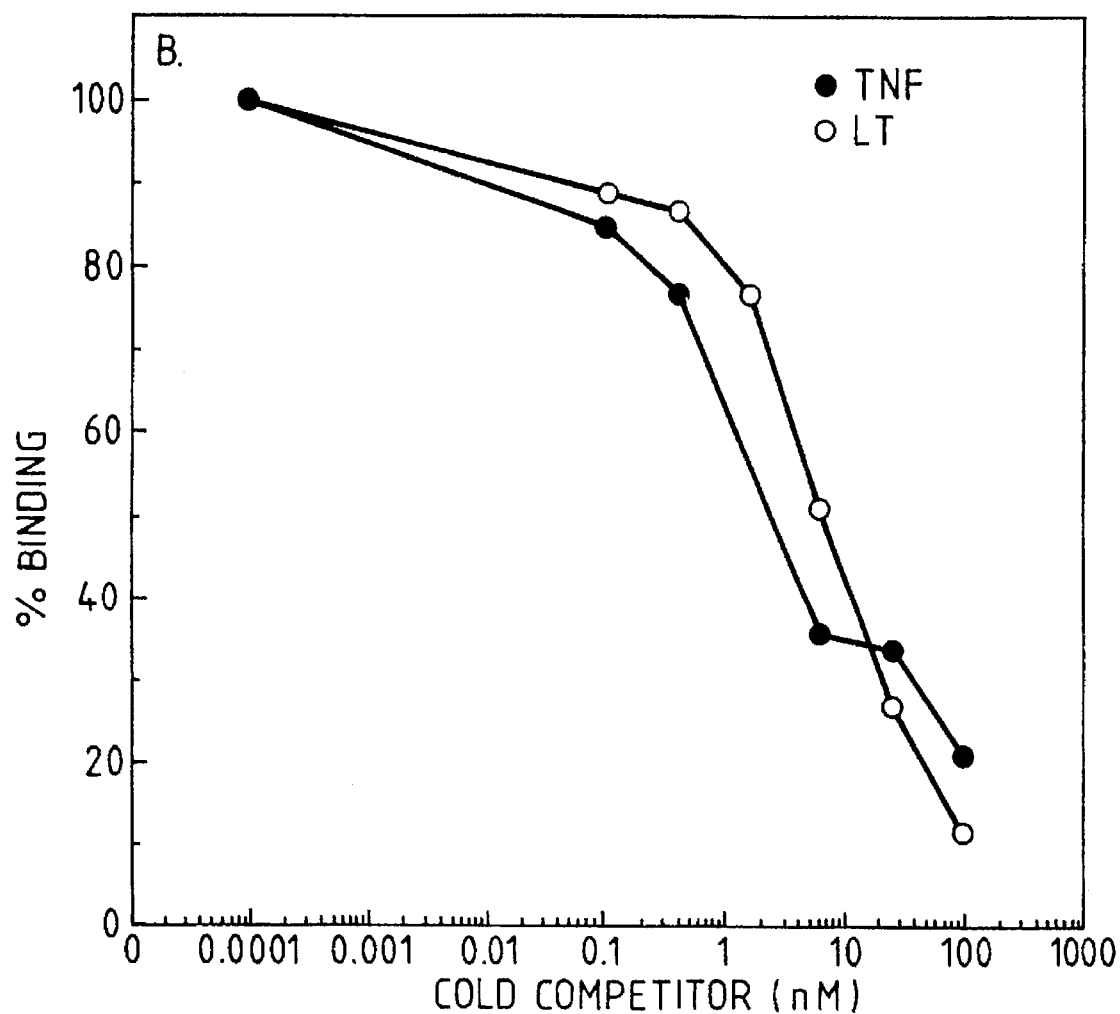

To confirm that the cDNA shown in FIG. 1 indeed encodes the TNF receptor, the cDNA was engineered for expression in mammalian cells. The cDNA contains an EcoRI site at position 1270 of FIG. 1. The receptor coding sequence was isolated as a 1300 bp EcoRI-fragment (containing all but the last 81 codons of the cytoplasmic domain) and inserted into a mammalian cell expression vector containing a cytomegalovirus promoter and SV40 transcription termination sequences (12). The resulting plasmid was transfected into COS cells which were analyzed for TNF receptor expression after three days. As shown in FIG. 3, the transfected cells specifically bound radioiodinated TNFα in a saturable and dose dependent fashion. The population of COS cells expressed approximately $1 \times 10^8$ receptors per cell. The measured binding affinity of recombinant receptors was $2.5 \times 10^9 M^{-1}$ at 4° C. which is in close agreement with natural receptor on human cells (19,20). The binding of $^{125}$I-TNFα (1 nM) to these cells could be inhibited by the addition of unlabelled TNFα or lymphotoxin (FIG. 3b). COS cells transfected with just the expression vector did not significantly bind $^{125}$I-TNFα (less than 2% of the binding seen with the cDNA transfection).

Figure 4A:
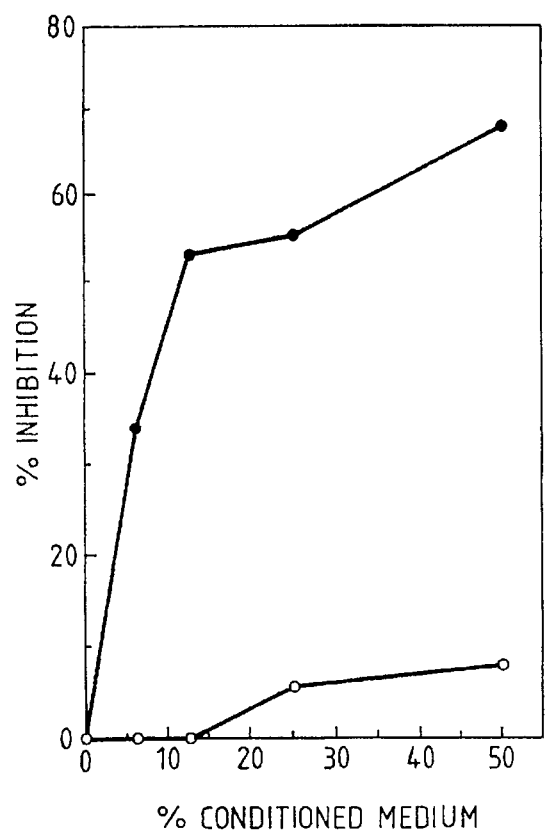
Figure 4B:
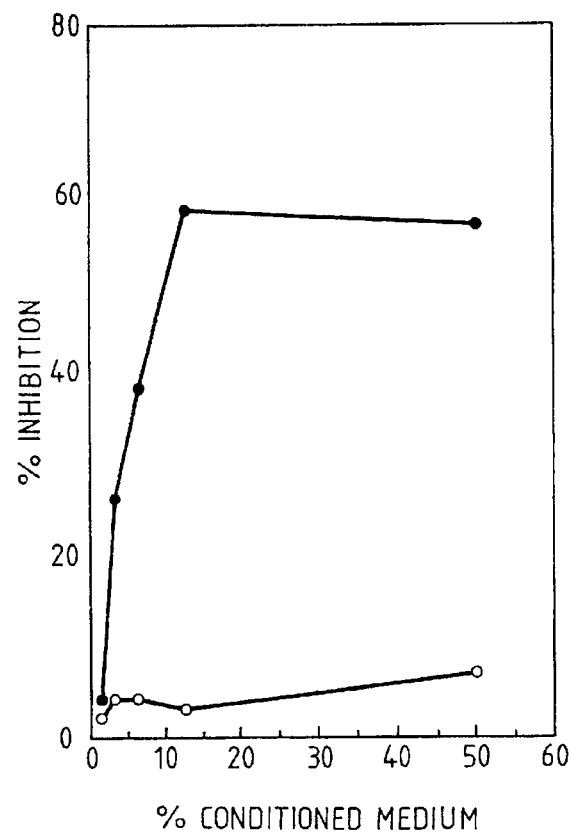

The extracellular domain of the TNF receptor is naturally shed from cells. To produce a similar recombinant derivative, a stop codon preceding the transmembrane domain was engineered into the cDNA by PCR mutagenesis. The modified DNA was inserted into the expression plasmid and subsequently transfected into COS cells. After three days, the COS cell media was tested for inhibition of TNFα binding to human U937 cells. As shown in FIG. 4a, the transfected cell media inhibited up to 70% of the binding of TNFα. The recombinant TNF receptor derivative was next tested for inhibition of TNFα biological activity. A sensitive bioassay for TNFα is a measurement of cytolysis of mouse WEHI 164 (clone 13) cells. The transfected cell media inhibited 60% of TNFα cytotoxicity on this cell line (FIG. 4b). Media from mock transfected COS cells did not inhibit TNFα induced cytotoxicity or binding. These experiments demonstrate that the recombinant extracellular domain of the TNF receptor is capable of binding TNF and inhibiting its biological activity.

Similarly the gel purified products of PCR's using 5' Cla and IIIA and IIIB and 5D were mixed and subjected to further amplification using 5' Cla and 5D as primers. This product was digested with BglII and HindIII and cloned into Bgl II/Hind III cut 5'-ΔCla to yield pΔIII. In all cases the cloned derivatives were analysed by restriction enzyme analysis and DNA sequencing using sequenase (United States Biochemical Corporation).

TABLE 1

Structure of the mutagenic oligonucleotides

| Oligo Name | Sequence | |
|---|---|---|
| 5'Cla | 5'-GTTCTATCGATAAGAGGCCATAGCTGTCTGGC-3' | (SEQ ID NO: 10) |
| IA | 5'-GCTCTCACACTCTCTCTTCTCCCTGTCCCCTAG-3' | (SEQ ID NO: 11) |
| IB | 5'-AGGGAGAAGAGAGAGTGTGAGAGCGGCTCCTTC-3' | (SEQ ID NO: 12) |
| IIIA | 5'-TGCATGGCAGGTACACACGGTGTCCGGTCCAC-3' | (SEQ ID NO: 13) |
| IIIB | 5'-GACACCGTGTGTACCTGCCATGCAGGTTTCTTT-3' | (SEQ ID NO: 14) |
| 4D | 5'-GGCCAAGCTTCAGGTGCACACGGTGTTCTG-3' | (SEQ ID NO: 15) |
| 5A | 5'-GCTGCTCCAAATGCCGAAAG-3' | (SEQ ID NO: 16) |
| 5D | 5'-AGTTCAAGCTTTACAGTGCCCTTAACATTCTAA-3' | (SEQ ID NO: 17) |

EXAMPLE 1

Expression of polypeptide consisting essentially of the first three cysteine-rich subdomains of the extracellular binding domain of the 55 kD receptor

1. MATERIALS AND METHODS

Reagents

E. coli derived recombinant human TNFα had a specific activity of 2×10$^7$ U/mg in an L929 cytotoxicity assay. Oligonucleotides were purchased from Oswel DNA service (University of Edinburgh).

Generation of the recombinant soluble TNFR derivatives

Figure 5:
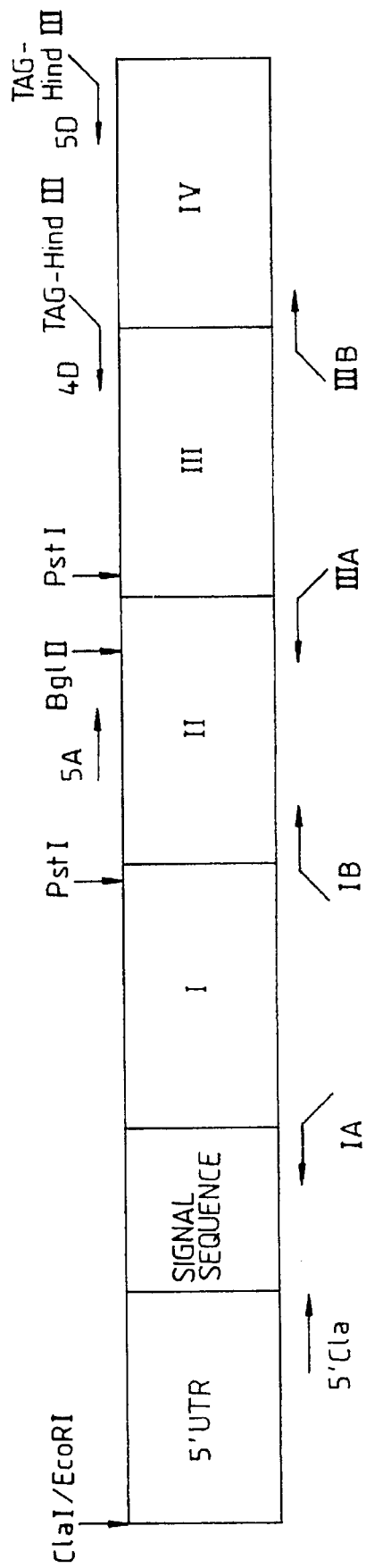
FIG. 5 is a diagram of the DNA sequence of pTNFRecd and is also a strategy map for polymerase chain reaction (PCR)-based domain deletion, in which 5'UTR is the 5'-untranslated region and I to IV are the four cysteine-rich subdomains. The oligonucleotides employed in PCR in the Example and relevant restriction sites are also shown.
Figure 6:
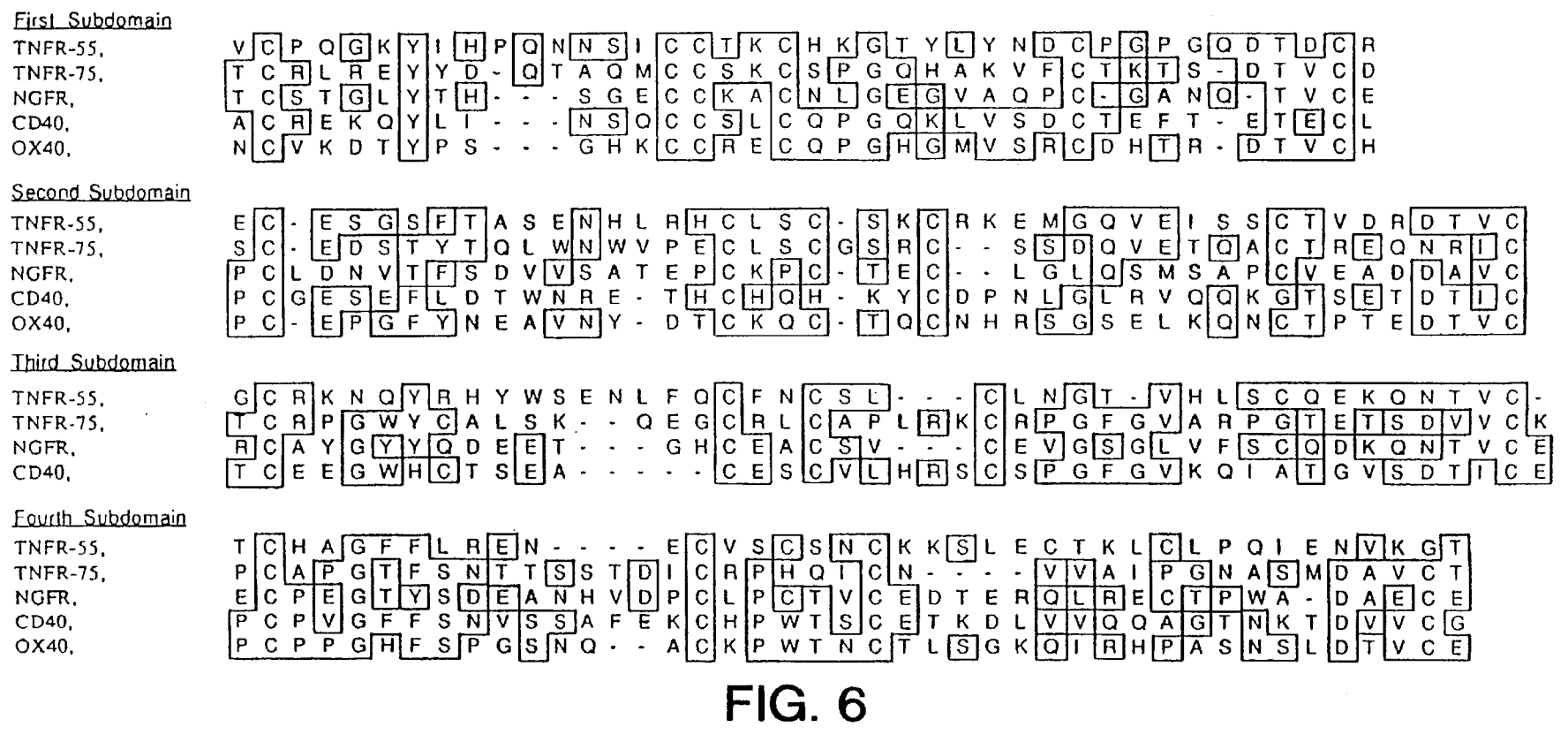

Deletion of each of the subdomains in the recombinant soluble TNFR was achieved by means of PCR fragment joining and PCR mutagenesis. The sequence of the oligonucleotides used in these experiments is given in Table 1 and their locations relative to the four cysteine rich subdomains is shown in FIG. 5. The four subdomains are lined up with respect to one another in FIG. 6.

The plasmid pTNFRecd (Reference Example) is shown in FIG. 7. pTNFRecd was further modified to remove 5' untranslated sequences by cloning of the Cla I/Bgl II digested product of a PCR using oligos 5' Cla and IIIA into ClaI/Bgl II digested pTNFRecd, to generate 5'-ΔCla. Digestion of 5'-ΔCla with Pst-1 and religation resulted in the generation of pΔII, which lacks the second cysteine rich subdomain (FIG. 9). The fourth cysteine rich subdomain was removed by cloning of the BglII/Hind III digested product of a PCR using oligonucleotides 5A and 4D into BglII/Hind III 5'-ΔCla; this introduced a termination codon after amino acid 167 (counting from the initial methionine) to yield pΔIV (FIG. 11). The constructs p I (FIG. 8) and pΔIII (FIG. 10) which lack the first and third cysteine rich subdomains respectively were generated by joining PCR fragments by means of overlaps introduced into the primers used for the PCR. The gel purified products of PCR's using 5' Cla and IA and IB and 5D were mixed and subjected to further amplification using 5' Cla and 5D as primers. The resulting fragment was digested with ClaI and BglII and cloned into ClaI/BglII digested pTNFRecd, to yield pΔI.

Analysis of recombinant soluble TNFR derivatives

COS cells were maintained in Dulbecco's modified Eagles medium containing 5% foetal calf serum. The soluble TNFα receptor derivatives were transfected into monkey COS cells by means of lipofectin (GIBCO-BRL, Bethesda Md.) according to the manufacturers protocol and cell free supernatants harvested 72 hours post transfection.

Inhibition of TNFα activity

The soluble TNFα receptor derivatives were analyzed for inhibition of TNFα cytotoxic activity in vitro. The cytotoxicity assay was performed as described on the TNFα sensitive cell line WEHI 164 clone 13. Serial dilutions of supernatants from COS cells transfected with the mutant receptors or mock transfected controls were incubated with a constant amount of TNF (1 ng/ml) for 1 hour at 37° C. before addition to the assay.

2. RESULTS

Figure 12A:
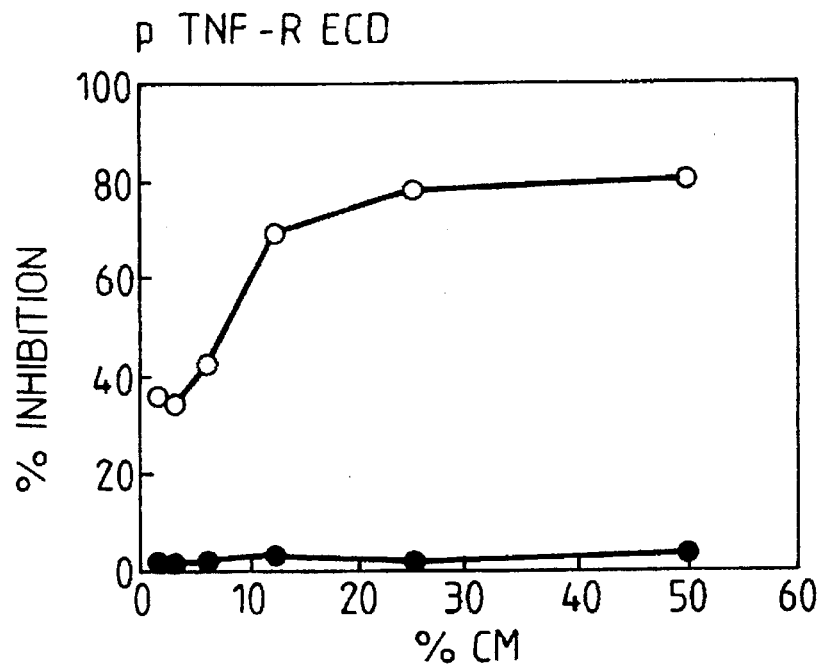
FIG. 12 shows the results of the assays described in the Example 1.
Figure 12B:
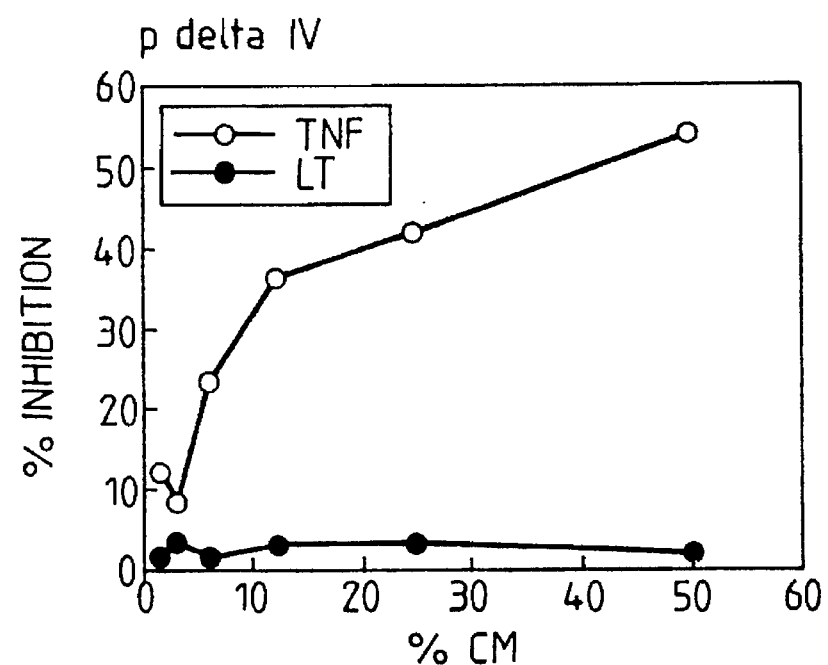

In order to understand more about the contribution of the individual cysteine rich subdomains to the binding of TNFα by the soluble form of the 55 kD TNF receptor, we removed each subdomain by PCR mutagenesis (FIG. 5). COS cells were transfected with each of these constructs and the supernatants were assayed for their ability to inhibit the cytotoxic activity of TNFα. FIG. 12 panel A shows that conditioned medium from COS cells tranfected with pTNFRecd inhibits TNFα as previously described. Removal of the fourth cysteine rich subdomain resulted in a protein which, similar to TNFRecd, was a potent inhibitor of TNFα (FIG. 12 panel B). The mutants lacking the first, second and third subdomains did not show any inhibitory activity in the TNFα cytotoxicity assay.

EXAMPLE 2

Expression of polypeptide consisting essentially of the first three cysteine-rich subdomains of the extracellular binding domain of the 75 kD receptor The coding region of the human 75 kD TNFα receptor was isolated from a T cell lambda ZAP library, using a probe based on published sequences (3) and cloned into the EcoRI site of a mammalian cell expression vector (12) resulting in plasmid p75TNFR. In more detail, RNA was extracted from a cell line expressing the 75 kD receptor and reverse transcribed. Any cell line expressing this receptor could be used, such as those described by Smith et al (3). The product of the reverse transcription was subjected to 25 cycles of PCR using the following primers: 5' CGC AGA ATT CCC CGC AGC CAT GGC GCC CGT CGC C 3' (SEQ ID NO: 18) and 5' GTA AGG ATC CTA TCG CCA GTG CTC CCT TCA GCT 3' (SEQ ID NO: 19).

These primers are directed against the extracellular binding domain coding region of the 75 kD receptor and were taken from Smith et al (3). The amplified product was gel purified and shown to encode TNFR. This was subsequently used to screen the library. Plaque purification was performed essentially as described in the Reference Example except that the probe was labelled by random priming (21) and hybridised in 50% formamide. Filters were washed in 0.2× SSC (Standard Saline Citrate) twice at 60° C.

Figure 13:
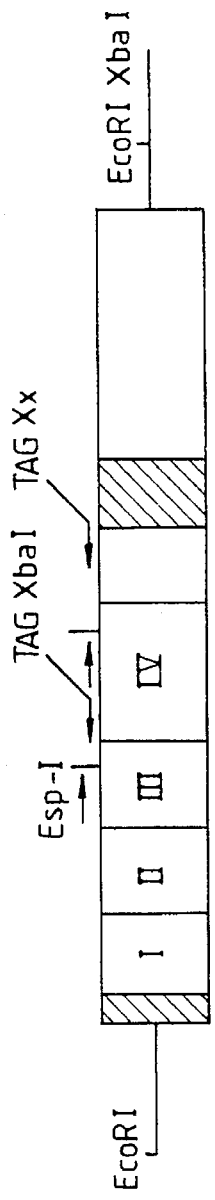
FIG. 13 shows diagrammatically the DNA encoding the 75 kD receptor in which I to IV are the four cysteine-rich subdomains. Oligonucleotides employed in PCR-domain deletion are also shown.

A derivative of the 75 kD TNFα receptor was produced by engineering a termination codon just prior to the transmembrane domain. Referring to FIG. 13, the polymerase chain reaction (PCR) technique was used to generate a 274 bp restriction fragment containing a BglII site at the 5' end and an Xba I site preceded by a TAG stop codon at the 3' end. The PCR primers were 5' ACACGACTTCATCCACG-GATA (SEQ ID NO: 20) and 5' ACGTTCTAGAC-TAGTCGCCAGTGCTCCCTTCAGCTG (SEQ ID NO: 21). The PCR product was digested with Bgl II and Xba I, gel purified and cloned into the TNF receptor expression plasmid (described above) digested with BglII and Xba I. DNA sequencing confirmed that the resulting plasmid contained the designed DNA sequence.

A similar approach was utilised to generate a construct which lacked the fourth cysteine-rich subdomain of the 75 kD TNFα receptor. PCR was performed using a primer upstream of the Esp I site in the 75 kD TNFR and a primer which introduced a TAG termination codon and an Xba I site. The sequences of the primers was 5' CAG AAC CGC ATC TGC ACC TGC (SEQ ID NO: 22) and 5' ACGTTCTA-GACTTGCACACCACGTCTGATGTTTC (SEQ ID NO: 23) respectively. The PCR product was digested with EspI and Xba I and the 110 bp DNA fragment gel purified and cloned into Esp I Xba I digested p75TNFR.

REFERENCES

1. Loetscher, H., Pan, Y.-C. E., Lahm, H.-W., Gentz, R., Brockhaus, M., Tabuchi, H. and Lesslayer, W. (1990) Cell, 61, 351–359.
2. Schall, T. J., Lewis, M., Koller, K. J., Lee, A., Rice, G. C., Wong, G. H. W., Gatanaga, T., Granger, G. A., Lentz, R., Raab, H., Kohl, W. J. and Goeddel, D. Y. (1990) Cell, 61, 361–370.
3. Smith, C. A., Davis, T., Anderson, D., Solam, L., Beckmann, M. P., Jerzy, R., Dower, S. K., Cosman, D. and Goodwin, R. G. (1990) Science 248, 1019–1023.
4. Ruff, M. R. & Gifford, G. E. (1981) Infection and Immunity, 31, 380.
5. Maniatis, T., Hardison, R. C., Lacy, E., Lauer, J., O'Connell, C., Quon, D., Sim, G. K. and Efstratiadis, A. (1978) Cell 15, 687–701.
6. Lawn, R. M., Fritsch, E. F., Parker, R. C., Blake, G & Maniatis, T. (1978) Cell 15, 1157–1174.
7. Gray, P. W., Leong, S. R., Fennie, E., Farrar, M. A., Pingel, J. T. and Schreiber, R. D. (1989) Proc. Natl. Acad. Sci USA 86, 8497–8501.
8. Smith, A. J. H., (1980) Meth. Enzym. 65 560–580.
9. Blin, N, & Stanford, D. W. (1976) Nucl. Acids Res. 3, 2303–2398.
10. Southern, E. M. (1975) J. Molec. Biol. 98, 503–517.
11. Dobner, P. R., Kawasaki, E. S., Yu, L. Y. and Bancroft, F. C. (1981) Proc. Natl. Acad. Sci. USA. 78, 2230–2234.
12. Eaton, D. L., Wood, W. I., Eaton, D., Hass, P. E., Hollinghead, P., Wion, K., Mather, J., Lawn, R. M., Vahar, G. A. and Gorman, C. (1986) Biochemistry 25: 8343–8347.
13. Scharf, S. J., Horn, G. T., Erlich, H. A. (1986) Science 233, 1076–1079.
14. Scatchard, G. (1949) Ann. New York Acad. Sci. 51, 660–672.
15. Espevik, T. & Nissen-Meyer, J. (1986) J. Immunol. Meths. 95, 99–105.
16. Kozak, M. (1989) J. Cell. Biol. 108, 229–241.
17. von Heijne, G. (1988) Nucl. Acids. Res. 14, 4683–4690.
18. Creasy, A. A., Yamamoto, R. & Vitt, C. R. (1987) Proc. Natl. Acad. Sci. USA. 84, 3293–3297.
19. Stauber, G. B., Alyer, R. A. & Aggarwal, B. B. (1988) J. Biol. Chem. 263, 19098–19104.
20. Scheurich, P., Ucer, U., Kronke, M. and Pfitzenmaier, K. (1986) Int. J. Cancer, 38, 127–133.
21. Feinburg, A. & Vogelstein, B (1984) Analytical Biochem. 137, 266–277.

SEQUENCE LISTING ( 1 ) GENERAL INFORMATION:

( i i i ) NUMBER OF SEQUENCES: 57

( 2 ) INFORMATION FOR SEQ ID NO: 1:

( i ) SEQUENCE CHARACTERISTICS:
        ( A ) LENGTH: 501 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..501

( x i ) SEQUENCE DESCRIPTION: SEQ ID NO: 1:

| | | | | | | | | | | | | | | | | |
|---|---|---|---|---|---|---|---|---|---|---|---|---|---|---|---|---|
| ATG | GGC | CTC | TCC | ACC | GTG | CCT | GAC | CTG | CTG | CTG | CCG | CTG | GTG | CTC | CTG | 48 |
| Met | Gly | Leu | Ser | Thr | Val | Pro | Asp | Leu | Leu | Leu | Pro | Leu | Val | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAG | CTG | TTG | GTG | GGA | ATA | TAC | CCC | TCA | GGG | GTT | ATT | GGA | CTG | GTC | CCT | 96 |
| Glu | Leu | Leu | Val | Gly | Ile | Tyr | Pro | Ser | Gly | Val | Ile | Gly | Leu | Val | Pro | |
| | | | | 20 | | | | | 25 | | | | | 30 | | |

| | | | | | | | | | | | | | | | | |
|---|---|---|---|---|---|---|---|---|---|---|---|---|---|---|---|---|
| CAC | CTA | GGG | GAC | AGG | GAG | AAG | AGA | GAT | AGT | GTG | TGT | CCC | CAA | GGA | AAA | 144 |
| His | Leu | Gly | Asp | Arg | Glu | Lys | Arg | Asp | Ser | Val | Cys | Pro | Gln | Gly | Lys | |
| | | | | 35 | | | | | 40 | | | | | 45 | | |

| | | | | | | | | | | | | | | | | |
|---|---|---|---|---|---|---|---|---|---|---|---|---|---|---|---|---|
| TAT | ATC | CAC | CCT | CAA | AAT | AAT | TCG | ATT | TGC | TGT | ACC | AAG | TGC | CAC | AAA | 192 |
| Tyr | Ile | His | Pro | Gln | Asn | Asn | Ser | Ile | Cys | Cys | Thr | Lys | Cys | His | Lys | |
| | | 50 | | | | | 55 | | | | | 60 | | | | |

| | | | | | | | | | | | | | | | | |
|---|---|---|---|---|---|---|---|---|---|---|---|---|---|---|---|---|
| GGA | ACC | TAC | TTG | TAC | AAT | GAC | TGT | CCA | GGC | CCG | GGG | CAG | GAT | ACG | GAC | 240 |
| Gly | Thr | Tyr | Leu | Tyr | Asn | Asp | Cys | Pro | Gly | Pro | Gly | Gln | Asp | Thr | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TGC | AGG | GAG | TGT | GAG | AGC | GGC | TCC | TTC | ACC | GCT | TCA | GAA | AAC | CAC | CTC | 288 |
| Cys | Arg | Glu | Cys | Glu | Ser | Gly | Ser | Phe | Thr | Ala | Ser | Glu | Asn | His | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| AGA | CAC | TGC | CTC | AGC | TGC | TCC | AAA | TGC | CGA | AAG | GAA | ATG | GGT | CAG | GTG | 336 |
| Arg | His | Cys | Leu | Ser | Cys | Ser | Lys | Cys | Arg | Lys | Glu | Met | Gly | Gln | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| GAG | ATC | TCT | TCT | TGC | ACA | GTG | GAC | CGG | GAC | ACC | GTG | TGT | GGC | TGC | AGG | 384 |
| Glu | Ile | Ser | Ser | Cys | Thr | Val | Asp | Arg | Asp | Thr | Val | Cys | Gly | Cys | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| AAG | AAC | CAG | TAC | CGG | CAT | TAT | TGG | AGT | GAA | AAC | CTT | TTC | CAG | TGC | TTC | 432 |
| Lys | Asn | Gln | Tyr | Arg | His | Tyr | Trp | Ser | Glu | Asn | Leu | Phe | Gln | Cys | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| AAT | TGC | AGC | CTC | TGC | CTC | AAT | GGG | ACC | GTG | CAC | CTC | TCC | TGC | CAG | GAG | 480 |
| Asn | Cys | Ser | Leu | Cys | Leu | Asn | Gly | Thr | Val | His | Leu | Ser | Cys | Gln | Glu | |
| 145 | | | | | 150 | | | | | 155 | | | | | 160 | |

| | | | | | | |
|---|---|---|---|---|---|---|
| AAA | CAG | AAC | ACC | GTG | TGC | ACC | 501 |
| Lys | Gln | Asn | Thr | Val | Cys | Thr | |
| | | | | 165 | | | |

( 2 ) INFORMATION FOR SEQ ID NO: 2:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | | |
|---|---|---|---|---|---|---|---|---|---|---|---|---|---|---|---|
| Met | Gly | Leu | Ser | Thr | Val | Pro | Asp | Leu | Leu | Leu | Pro | Leu | Val | Leu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Glu | Leu | Leu | Val | Gly | Ile | Tyr | Pro | Ser | Gly | Val | Ile | Gly | Leu | Val | Pro |
| | | | | 20 | | | | | 25 | | | | | 30 | |

| | | | | | | | | | | | | | | | |
|---|---|---|---|---|---|---|---|---|---|---|---|---|---|---|---|
| His | Leu | Gly | Asp | Arg | Glu | Lys | Arg | Asp | Ser | Val | Cys | Pro | Gln | Gly | Lys |
| | | | | 35 | | | | | 40 | | | | | 45 | |

| | | | | | | | | | | | | | | | |
|---|---|---|---|---|---|---|---|---|---|---|---|---|---|---|---|
| Tyr | Ile | His | Pro | Gln | Asn | Asn | Ser | Ile | Cys | Cys | Thr | Lys | Cys | His | Lys |
| | | 50 | | | | | 55 | | | | | 60 | | | |

| | | | | | | | | | | | | | | | |
|---|---|---|---|---|---|---|---|---|---|---|---|---|---|---|---|
| Gly | Thr | Tyr | Leu | Tyr | Asn | Asp | Cys | Pro | Gly | Pro | Gly | Gln | Asp | Thr | Asp |
| 65 | | | | | 70 | | | | | 75 | | | | | 80 |

| | | | | | | | | | | | | | | | |
|---|---|---|---|---|---|---|---|---|---|---|---|---|---|---|---|
| Cys | Arg | Glu | Cys | Glu | Ser | Gly | Ser | Phe | Thr | Ala | Ser | Glu | Asn | His | Leu |
| | | | | 85 | | | | | 90 | | | | | 95 | |

| | | | | | | | | | | | | | | | |
|---|---|---|---|---|---|---|---|---|---|---|---|---|---|---|---|
| Arg | His | Cys | Leu | Ser | Cys | Ser | Lys | Cys | Arg | Lys | Glu | Met | Gly | Gln | Val |
| | | | 100 | | | | | 105 | | | | | 110 | | |

| | | | | | | | | | | | | | | | |
|---|---|---|---|---|---|---|---|---|---|---|---|---|---|---|---|
| Glu | Ile | Ser | Ser | Cys | Thr | Val | Asp | Arg | Asp | Thr | Val | Cys | Gly | Cys | Arg |

|  |  |  |  |  |  |  |  |  |  |  |  |  |  |  |  |
|---|---|---|---|---|---|---|---|---|---|---|---|---|---|---|---|
|  |  | 115 |  |  |  |  | 120 |  |  |  |  |  | 125 |  |  |
| Lys | Asn<br>130 | Gln | Tyr | Arg | His | Tyr<br>135 | Trp | Ser | Glu | Asn | Leu<br>140 | Phe | Gln | Cys | Phe |
| Asn<br>145 | Cys | Ser | Leu | Cys | Leu<br>150 | Asn | Gly | Thr | Val | His<br>155 | Leu | Ser | Cys | Gln | Glu<br>160 |
| Lys | Gln | Asn | Thr | Val<br>165 | Cys | Thr |  |  |  |  |  |  |  |  |  |

( 2 ) INFORMATION FOR SEQ ID NO: 3:

( i ) SEQUENCE CHARACTERISTICS:
    ( A ) LENGTH: 372 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 1..372

( x i ) SEQUENCE DESCRIPTION: SEQ ID NO: 3:

| GTG | TGT | CCC | CAA | GGA | AAA | TAT | ATC | CAC | CCT | CAA | AAT | AAT | TCG | ATT | TGC | 48 |
|---|---|---|---|---|---|---|---|---|---|---|---|---|---|---|---|---|
| Val<br>1 | Cys | Pro | Gln | Gly<br>5 | Lys | Tyr | Ile | His | Pro<br>10 | Gln | Asn | Asn | Ser | Ile<br>15 | Cys |  |
| TGT | ACC | AAG | TGC | CAC | AAA | GGA | ACC | TAC | TTG | TAC | AAT | GAC | TGT | CCA | GGC | 96 |
| Cys | Thr | Lys | Cys<br>20 | His | Lys | Gly | Thr | Tyr<br>25 | Leu | Tyr | Asn | Asp | Cys<br>30 | Pro | Gly |  |
| CCG | GGG | CAG | GAT | ACG | GAC | TGC | AGG | GAG | TGT | GAG | AGC | GGC | TCC | TTC | ACC | 144 |
| Pro | Gly | Gln<br>35 | Asp | Thr | Asp | Cys | Arg<br>40 | Glu | Cys | Glu | Ser | Gly<br>45 | Ser | Phe | Thr |  |
| GCT | TCA | GAA | AAC | CAC | CTC | AGA | CAC | TGC | CTC | AGC | TGC | TCC | AAA | TGC | CGA | 192 |
| Ala | Ser<br>50 | Glu | Asn | His | Leu | Arg<br>55 | His | Cys | Leu | Ser | Cys<br>60 | Ser | Lys | Cys | Arg |  |
| AAG | GAA | ATG | GGT | CAG | GTG | GAG | ATC | TCT | TCT | TGC | ACA | GTG | GAC | CGG | GAC | 240 |
| Lys<br>65 | Glu | Met | Gly | Gln | Val<br>70 | Glu | Ile | Ser | Ser | Cys<br>75 | Thr | Val | Asp | Arg | Asp<br>80 |  |
| ACC | GTG | TGT | GGC | TGC | AGG | AAG | AAC | CAG | TAC | CGG | CAT | TAT | TGG | AGT | GAA | 288 |
| Thr | Val | Cys | Gly | Cys<br>85 | Arg | Lys | Asn | Gln | Tyr<br>90 | Arg | His | Tyr | Trp | Ser<br>95 | Glu |  |
| AAC | CTT | TTC | CAG | TGC | TTC | AAT | TGC | AGC | CTC | TGC | CTC | AAT | GGG | ACC | GTG | 336 |
| Asn | Leu | Phe | Gln<br>100 | Cys | Phe | Asn | Cys | Ser<br>105 | Leu | Cys | Leu | Asn | Gly<br>110 | Thr | Val |  |
| CAC | CTC | TCC | TGC | CAG | GAG | AAA | CAG | AAC | ACC | GTG | TGC |  |  |  |  | 372 |
| His | Leu | Ser<br>115 | Cys | Gln | Glu | Lys | Gln<br>120 | Asn | Thr | Val | Cys |  |  |  |  |  |

( 2 ) INFORMATION FOR SEQ ID NO: 4:

( i ) SEQUENCE CHARACTERISTICS:
    ( A ) LENGTH: 124 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 4:

| Val<br>1 | Cys | Pro | Gln | Gly<br>5 | Lys | Tyr | Ile | His | Pro<br>10 | Gln | Asn | Asn | Ser | Ile<br>15 | Cys |
|---|---|---|---|---|---|---|---|---|---|---|---|---|---|---|---|
| Cys | Thr | Lys | Cys<br>20 | His | Lys | Gly | Thr | Tyr<br>25 | Leu | Tyr | Asn | Asp | Cys<br>30 | Pro | Gly |
| Pro | Gly | Gln<br>35 | Asp | Thr | Asp | Cys | Arg<br>40 | Glu | Cys | Glu | Ser | Gly<br>45 | Ser | Phe | Thr |

```
Ala  Ser  Glu  Asn  His  Leu  Arg  His  Cys  Leu  Ser  Cys  Ser  Lys  Cys  Arg
     50                       55                 60

Lys  Glu  Met  Gly  Gln  Val  Glu  Ile  Ser  Ser  Cys  Thr  Val  Asp  Arg  Asp
65                       70                      75                           80

Thr  Val  Cys  Gly  Cys  Arg  Lys  Asn  Gln  Tyr  Arg  His  Tyr  Trp  Ser  Glu
                    85                       90                       95

Asn  Leu  Phe  Gln  Cys  Phe  Asn  Cys  Ser  Leu  Cys  Leu  Asn  Gly  Thr  Val
               100                      105                      110

His  Leu  Ser  Cys  Gln  Glu  Lys  Gln  Asn  Thr  Val  Cys
               115                 120
```

( 2 ) INFORMATION FOR SEQ ID NO: 5:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

```
Glu  Met  Gly  Gln  Val  Glu  Ile  Ser  Ser  Thr  Val  Asp  Arg  Asp  Thr  Val
 1                       5                      10                           15

Cys  Gly
```

( 2 ) INFORMATION FOR SEQ ID NO: 6:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

AAGGAGATGG GCCAGGTTGA GATCTCTTCT ACTGTTGACA ATGACACTGT GTGTGGC    57

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 7:

GCTGCTCCAA ATGCCGAAAG    20

( 2 ) INFORMATION FOR SEQ ID NO: 8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 8:

AGTTCAAGCT TTTACAGTGC CCTTAACATT CTAA    34

( 2 ) INFORMATION FOR SEQ ID NO: 9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 9:

```
Asp  Arg  Glu  Lys  Arg
 1                    5
```

( 2 ) INFORMATION FOR SEQ ID NO: 10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 10:

GTTCTATCGA TAAGAGGCCA TAGCTGTCTG GC        32

( 2 ) INFORMATION FOR SEQ ID NO: 11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 11:

GCTCTCACAC TCTCTCTTCT CCCTGTCCCC TAG        33

( 2 ) INFORMATION FOR SEQ ID NO: 12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 12:

AGGGAGAAGA GAGAGTGTGA GAGCGGCTCC TTC        33

( 2 ) INFORMATION FOR SEQ ID NO: 13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 13:

TGCATGGCAG GTACACACGG TGTCCGGTC CAC        33

( 2 ) INFORMATION FOR SEQ ID NO: 14:

( i ) SEQUENCE CHARACTERISTICS:
        ( A ) LENGTH: 33 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 14:

GACACCGTGT GTACCTGCCA TGCAGGTTTC TTT    33

( 2 ) INFORMATION FOR SEQ ID NO: 15:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 15:

GGCCAAGCTT CAGGTGCACA CGGTGTTCTG    30

( 2 ) INFORMATION FOR SEQ ID NO: 16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 16:

GCTGCTCCAA ATGCCGAAAG    20

( 2 ) INFORMATION FOR SEQ ID NO: 17:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 17:

AGTTCAAGCT TTACAGTGCC CTTAACATTC TAA    33

( 2 ) INFORMATION FOR SEQ ID NO: 18:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 18:

CGCAGAATTC CCCGCAGCCA TGGCGCCCGT CGCC    34

( 2 ) INFORMATION FOR SEQ ID NO: 19:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 19:

GTAAGGATCC TATCGCCAGT GCTCCCTTCA GCT    33

( 2 ) INFORMATION FOR SEQ ID NO: 20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 20:

ACACGACTTC ATCCACGGAT A    21

( 2 ) INFORMATION FOR SEQ ID NO: 21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 21:

ACGTTCTAGA CTAGTCGCCA GTGCTCCCTT CAGCTG    36

( 2 ) INFORMATION FOR SEQ ID NO: 22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 22:

CAGAACCGCA TCTGCACCTG C    21

( 2 ) INFORMATION FOR SEQ ID NO: 23:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 23:

ACGTTCTAGA CTTGCACACC ACGTCTGATG TTTC    34

( 2 ) INFORMATION FOR SEQ ID NO: 24:

( i ) SEQUENCE CHARACTERISTICS:
        ( A ) LENGTH: 2062 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 155..1519

( x i ) SEQUENCE DESCRIPTION: SEQ ID NO: 24:

```
ACCAGTGATC TCTATGCCCG AGTCTCAACC CTCAACTGTC ACCCCAAGGC ACTTGGGACG      60

TCCTGGACAG ACCGAGTCCC GGGAAGCCCC AGCACTGCCG CTGCCACACT GCCCTGAGCC     120

CAAATGGGGG AGTGAGAGGC CATAGCTGTC TGGC ATG GGC CTC TCC ACC GTG         172
                                      Met Gly Leu Ser Thr Val
                                       1               5

CCT GAC CTG CTG CTG CCG CTG GTG CTC CTG GAG CTG TTG GTG GGA ATA      220
Pro Asp Leu Leu Leu Pro Leu Val Leu Leu Glu Leu Leu Val Gly Ile
         10                  15                  20

TAC CCC TCA GGG GTT ATT GGA CTG GTC CCT CAC CTA GGG GAC AGG GAG      268
Tyr Pro Ser Gly Val Ile Gly Leu Val Pro His Leu Gly Asp Arg Glu
             25                  30                  35

AAG AGA GAT AGT GTG TGT CCC CAA GGA AAA TAT ATC CAC CCT CAA AAT      316
Lys Arg Asp Ser Val Cys Pro Gln Gly Lys Tyr Ile His Pro Gln Asn
         40                  45                  50

AAT TCG ATT TGC TGT ACC AAG TGC CAC AAA GGA ACC TAC TTG TAC AAT      364
Asn Ser Ile Cys Cys Thr Lys Cys His Lys Gly Thr Tyr Leu Tyr Asn
 55                  60                  65                  70

GAC TGT CCA GGC CCG GGG CAG GAT ACG GAC TGC AGG GAG TGT GAG AGC      412
Asp Cys Pro Gly Pro Gly Gln Asp Thr Asp Cys Arg Glu Cys Glu Ser
             75                  80                  85

GGC TCC TTC ACC GCT TCA GAA AAC CAC CTC AGA CAC TGC CTC AGC TGC      460
Gly Ser Phe Thr Ala Ser Glu Asn His Leu Arg His Cys Leu Ser Cys
             90                  95                 100

TCC AAA TGC CGA AAG GAA ATG GGT CAG GTG GAG ATC TCT TCT TGC ACA      508
Ser Lys Cys Arg Lys Glu Met Gly Gln Val Glu Ile Ser Ser Cys Thr
        105                 110                 115

GTG GAC CGG GAC ACC GTG TGT GGC TGC AGG AAG AAC CAG TAC CGG CAT      556
Val Asp Arg Asp Thr Val Cys Gly Cys Arg Lys Asn Gln Tyr Arg His
    120                 125                 130

TAT TGG AGT GAA AAC CTT TTC CAG TGC TTC AAT TGC AGC CTC TGC CTC      604
Tyr Trp Ser Glu Asn Leu Phe Gln Cys Phe Asn Cys Ser Leu Cys Leu
135                 140                 145                 150

AAT GGG ACC GTG CAC CTC TCC TGC CAG GAG AAA CAG AAC ACC GTG TGC      652
Asn Gly Thr Val His Leu Ser Cys Gln Glu Lys Gln Asn Thr Val Cys
            155                 160                 165

ACC TGC CAT GCA GGT TTC TTT CTA AGA GAA AAC GAG TGT GTC TCC TGT      700
Thr Cys His Ala Gly Phe Phe Leu Arg Glu Asn Glu Cys Val Ser Cys
            170                 175                 180

AGT AAC TGT AAG AAA AGC CTG GAG TGC ACG AAG TTG TGC CTA CCC CAG      748
Ser Asn Cys Lys Lys Ser Leu Glu Cys Thr Lys Leu Cys Leu Pro Gln
        185                 190                 195

ATT GAG AAT GTT AAG GGC ACT GAG GAC TCA GGC ACC ACA GTG CTG TTG      796
Ile Glu Asn Val Lys Gly Thr Glu Asp Ser Gly Thr Thr Val Leu Leu
    200                 205                 210

CCC CTG GTC ATT TTC TTT GGT CTT TGC CTT TTA TCC CTC CTC TTC ATT      844
Pro Leu Val Ile Phe Phe Gly Leu Cys Leu Leu Ser Leu Leu Phe Ile
215                 220                 225                 230

GGT TTA ATG TAT CGC TAC CAA CGG TGG AAG TCC AAG CTC TAC TCC ATT      892
Gly Leu Met Tyr Arg Tyr Gln Arg Trp Lys Ser Lys Leu Tyr Ser Ile
            235                 240                 245

GTT TGT GGG AAA TCG ACA CCT GAA AAA GAG GGG GAG CTT GAA GGA ACT      940
Val Cys Gly Lys Ser Thr Pro Glu Lys Glu Gly Glu Leu Glu Gly Thr
            250                 255                 260

ACT ACT AAG CCC CTG GCC CCA AAC CCA AGC TTC AGT CCC ACT CCA GGC      988
Thr Thr Lys Pro Leu Ala Pro Asn Pro Ser Phe Ser Pro Thr Pro Gly
        265                 270                 275

TTC ACC CCC ACC CTG GGC TTC AGT CCC GTG CCC AGT TCC ACC TTC ACC     1036
```

```
Phe  Thr  Pro  Thr  Leu  Gly  Phe  Ser  Pro  Val  Pro  Ser  Ser  Thr  Phe  Thr
     280                 285                 290

TCC  AGC  TCC  ACC  TAT  ACC  CCC  GGT  GAC  TGT  CCC  AAC  TTT  GCG  GCT  CCC     1084
Ser  Ser  Ser  Thr  Tyr  Thr  Pro  Gly  Asp  Cys  Pro  Asn  Phe  Ala  Ala  Pro
295                      300                 305                      310

CGC  AGA  GAG  GTG  GCA  CCA  CCC  TAT  CAG  GGG  GCT  GAC  CCC  ATC  CTT  GCG     1132
Arg  Arg  Glu  Val  Ala  Pro  Pro  Tyr  Gln  Gly  Ala  Asp  Pro  Ile  Leu  Ala
                    315                 320                           325

ACA  GCC  CTC  GCC  TCC  GAC  CCC  ATC  CCC  AAC  CCC  CTT  CAG  AAG  TGG  GAG     1180
Thr  Ala  Leu  Ala  Ser  Asp  Pro  Ile  Pro  Asn  Pro  Leu  Gln  Lys  Trp  Glu
               330                      335                 340

GAC  AGT  GCC  CAC  AAG  CCA  CAG  AGC  CTA  GAC  ACT  GAT  GAC  CCC  CGG  ACG     1228
Asp  Ser  Ala  His  Lys  Pro  Gln  Ser  Leu  Asp  Thr  Asp  Asp  Pro  Arg  Thr
          345                 350                      355

CTG  TAC  GCC  GTG  GTG  GAG  AAC  GTG  CCC  CCG  TTG  CGC  TGG  AAG  GAA  TTC     1276
Leu  Tyr  Ala  Val  Val  Glu  Asn  Val  Pro  Pro  Leu  Arg  Trp  Lys  Glu  Phe
     360                 365                      370

GTG  CGG  CGC  CTA  GGG  CTG  AGC  GAC  CAC  GAG  ATC  GAT  CGG  CTG  GAG  CTG     1324
Val  Arg  Arg  Leu  Gly  Leu  Ser  Asp  His  Glu  Ile  Asp  Arg  Leu  Glu  Leu
375                      380                 385                           390

CAG  AAC  GGG  CGC  TGC  CTG  CGC  GAG  GCG  CAA  TAC  AGC  ATG  CTG  GCG  ACC     1372
Gln  Asn  Gly  Arg  Cys  Leu  Arg  Glu  Ala  Gln  Tyr  Ser  Met  Leu  Ala  Thr
               395                 400                           405

TGG  AGG  CGG  CGC  ACG  CCG  CGG  CGC  GAG  GCC  ACG  CTG  GAG  CTG  CTG  GGA     1420
Trp  Arg  Arg  Arg  Thr  Pro  Arg  Arg  Glu  Ala  Thr  Leu  Glu  Leu  Leu  Gly
               410                 415                           420

CGC  GTG  CTC  CGC  GAC  ATG  GAC  CTG  CTG  GGC  TGC  CTG  GAG  GAC  ATC  GAG     1468
Arg  Val  Leu  Arg  Asp  Met  Asp  Leu  Leu  Gly  Cys  Leu  Glu  Asp  Ile  Glu
          425                 430                      435

GAG  GCG  CTT  TGC  GGC  CCC  GCC  GCG  CTC  CCG  CCC  GCG  CCC  AGT  CTT  CTC     1516
Glu  Ala  Leu  Cys  Gly  Pro  Ala  Ala  Leu  Pro  Pro  Ala  Pro  Ser  Leu  Leu
440                      445                      450

AGA  TGAGGCTGCG  CCCTGCGGGC  AGCTCTAAGG  ACCGTCCTCG  CAGATCGCCT                    1569
Arg
455

TCCAACCCCA  CTTTTTTCTG  GAAAGGAGGG  GTCCTGCAGG  GGCAAGCAGG  AGCTAGCAGC     1629
CGCCTACTTG  GTGCTAACCC  CTCGATGTAC  ATAGCTTTTC  TCAGCTGCCT  GCGCGCCGCC     1689
GACAGTCAGC  GCTGTGCGCG  CGGAGAGAGG  TGCGCCGTGG  GCTCAAGAGC  CTGAGTGGGT     1749
GGTTTGCGAG  GATGAGGGAC  GCTATGCCTC  ATGCCCGTTT  TGGGTGTCCT  CACCAGCAAG     1809
GCTGCTCGGG  GGCCCCTGGT  TCGTCCCTGA  GCCTTTTTCA  CAGTGCATAA  GCAGTTTTTT     1869
TTGTTTTTGT  TTGTTTTGT   TTGTTTTTA   AATCAATCAT  GTTACACTAA  TAGAAACTTG     1929
GCACTCCTGT  GCCCTCTGCC  TGGACAAGCA  CATAGCAAGC  TGAACTGTCC  TAAGGCAGGG     1989
GCGAGCACGG  AACAATGGGG  CCTTCAGCTG  GAGCTGTGGA  CTTTTGTACA  TACACTAAAA     2049
TTCTGAAGTT  AAG                                                            2062
```

( 2 ) INFORMATION FOR SEQ ID NO: 25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 25:

```
Met  Gly  Leu  Ser  Thr  Val  Pro  Asp  Leu  Leu  Leu  Pro  Leu  Val  Leu  Leu
1                   5                   10                      15
```

-continued

| | | | | | | | | | | | | | |
|---|---|---|---|---|---|---|---|---|---|---|---|---|---|
|Glu|Leu|Leu|Val 20|Gly|Ile|Tyr|Pro|Ser 25|Gly|Val|Ile|Gly|Leu 30|Val|Pro|
|His|Leu|Gly 35|Asp|Arg|Glu|Lys|Arg 40|Asp|Ser|Val|Cys|Pro 45|Gln|Gly|Lys|
|Tyr|Ile 50|His|Pro|Gln|Asn|Asn 55|Ser|Ile|Cys|Cys|Thr 60|Lys|Cys|His|Lys|
|Gly 65|Thr|Tyr|Leu|Tyr|Asn 70|Asp|Cys|Pro|Gly|Pro 75|Gly|Gln|Asp|Thr|Asp 80|
|Cys|Arg|Glu|Cys|Glu 85|Ser|Gly|Ser|Phe|Thr 90|Ala|Ser|Glu|Asn|His 95|Leu|
|Arg|His|Cys|Leu 100|Ser|Cys|Ser|Lys|Cys 105|Arg|Lys|Glu|Met|Gly 110|Gln|Val|
|Glu|Ile|Ser 115|Ser|Cys|Thr|Val|Asp 120|Arg|Asp|Thr|Val|Cys 125|Gly|Cys|Arg|
|Lys|Asn 130|Gln|Tyr|Arg|His|Tyr 135|Trp|Ser|Glu|Asn|Leu 140|Phe|Gln|Cys|Phe|
|Asn 145|Cys|Ser|Leu|Cys|Leu 150|Asn|Gly|Thr|Val|His 155|Leu|Ser|Cys|Gln|Glu 160|
|Lys|Gln|Asn|Thr|Val 165|Cys|Thr|Cys|His|Ala 170|Gly|Phe|Phe|Leu|Arg 175|Glu|
|Asn|Glu|Cys|Val 180|Ser|Cys|Ser|Asn|Cys 185|Lys|Lys|Ser|Leu|Glu 190|Cys|Thr|
|Lys|Leu|Cys 195|Leu|Pro|Gln|Ile|Glu 200|Asn|Val|Lys|Gly|Thr 205|Glu|Asp|Ser|
|Gly|Thr 210|Thr|Val|Leu|Leu|Pro 215|Leu|Val|Ile|Phe|Phe 220|Gly|Leu|Cys|Leu|
|Leu 225|Ser|Leu|Leu|Phe|Ile 230|Gly|Leu|Met|Tyr|Arg 235|Tyr|Gln|Arg|Trp|Lys 240|
|Ser|Lys|Leu|Tyr|Ser 245|Ile|Val|Cys|Gly|Lys 250|Ser|Thr|Pro|Glu|Lys 255|Glu|
|Gly|Glu|Leu|Glu 260|Gly|Thr|Thr|Thr|Lys 265|Pro|Leu|Ala|Pro|Asn 270|Pro|Ser|
|Phe|Ser|Pro 275|Thr|Pro|Gly|Phe|Thr 280|Pro|Thr|Leu|Gly|Phe 285|Ser|Pro|Val|
|Pro|Ser 290|Ser|Thr|Phe|Thr|Ser 295|Ser|Ser|Thr|Tyr|Thr 300|Pro|Gly|Asp|Cys|
|Pro 305|Asn|Phe|Ala|Ala|Pro 310|Arg|Arg|Glu|Val|Ala 315|Pro|Pro|Tyr|Gln|Gly 320|
|Ala|Asp|Pro|Ile|Leu 325|Ala|Thr|Ala|Leu|Ala 330|Ser|Asp|Pro|Ile|Pro 335|Asn|
|Pro|Leu|Gln|Lys 340|Trp|Glu|Asp|Ser|Ala 345|His|Lys|Pro|Gln|Ser 350|Leu|Asp|
|Thr|Asp|Asp 355|Pro|Arg|Thr|Leu|Tyr 360|Ala|Val|Val|Glu|Asn 365|Val|Pro|Pro|
|Leu|Arg 370|Trp|Lys|Glu|Phe|Val 375|Arg|Arg|Leu|Gly|Leu 380|Ser|Asp|His|Glu|
|Ile 385|Asp|Arg|Leu|Glu|Leu 390|Gln|Asn|Gly|Arg|Cys 395|Leu|Arg|Glu|Ala|Gln 400|
|Tyr|Ser|Met|Leu|Ala 405|Thr|Trp|Arg|Arg|Arg 410|Thr|Pro|Arg|Arg|Glu 415|Ala|
|Thr|Leu|Glu|Leu|Leu 420|Gly|Arg|Val|Leu|Arg 425|Asp|Met|Asp|Leu|Leu 430|Gly|
|Cys|Leu|Glu|Asp|Ile|Glu|Glu|Ala|Leu|Cys|Gly|Pro|Ala|Ala|Leu|Pro|

435                    440                         445

Pro  Ala  Pro  Ser  Leu  Leu  Arg
450                           455

( 2 ) INFORMATION FOR SEQ ID NO: 26:

( i ) SEQUENCE CHARACTERISTICS:
            ( A ) LENGTH: 40 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 26:

Val  Cys  Pro  Gln  Gly  Lys  Tyr  Ile  His  Pro  Gln  Asn  Asn  Ser  Ile  Cys
1                   5                        10                            15

Cys  Thr  Lys  Cys  His  Lys  Gly  Thr  Tyr  Leu  Tyr  Asn  Asp  Cys  Pro  Gly
                20                       25                       30

Pro  Gly  Gln  Asp  Thr  Asp  Cys  Arg
          35                    40

( 2 ) INFORMATION FOR SEQ ID NO: 27:

( i ) SEQUENCE CHARACTERISTICS:
            ( A ) LENGTH: 38 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 27:

Thr  Cys  Arg  Leu  Arg  Glu  Tyr  Tyr  Asp  Gln  Thr  Ala  Gln  Met  Cys  Cys
1                   5                        10                            15

Ser  Lys  Cys  Ser  Pro  Gly  Gln  His  Ala  Lys  Val  Phe  Cys  Thr  Lys  Thr
                20                       25                       30

Ser  Asp  Thr  Val  Cys  Asp
          35

( 2 ) INFORMATION FOR SEQ ID NO: 28:

( i ) SEQUENCE CHARACTERISTICS:
            ( A ) LENGTH: 35 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO: 28:

Thr  Cys  Ser  Thr  Gly  Leu  Tyr  Thr  His  Ser  Gly  Glu  Cys  Cys  Lys  Ala
1                   5                        10                            15

Cys  Asn  Leu  Gly  Glu  Gly  Val  Ala  Gln  Pro  Cys  Gly  Ala  Asn  Gln  Thr
                20                       25                       30

Val  Cys  Glu
          35

( 2 ) INFORMATION FOR SEQ ID NO: 29:

( i ) SEQUENCE CHARACTERISTICS:
            ( A ) LENGTH: 36 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 29:

```
Ala  Cys  Arg  Glu  Lys  Gln  Tyr  Leu  Ile  Asn  Ser  Gln  Cys  Cys  Ser  Leu
 1              5                        10                       15

Cys  Gln  Pro  Gly  Gln  Lys  Leu  Val  Ser  Asp  Cys  Thr  Glu  Phe  Thr  Glu
              20                        25                       30

Thr  Glu  Cys  Leu
              35
```

( 2 ) INFORMATION FOR SEQ ID NO: 30:

( i ) SEQUENCE CHARACTERISTICS:
  ( A ) LENGTH: 36 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 30:

```
Asn  Cys  Val  Lys  Asp  Thr  Tyr  Pro  Ser  Gly  His  Lys  Cys  Cys  Arg  Glu
 1              5                        10                       15

Cys  Gln  Pro  Gly  His  Gly  Met  Val  Ser  Arg  Cys  Asp  His  Thr  Arg  Asp
              20                        25                       30

Thr  Val  Cys  His
              35
```

( 2 ) INFORMATION FOR SEQ ID NO: 31:

( i ) SEQUENCE CHARACTERISTICS:
  ( A ) LENGTH: 43 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 31:

```
Glu  Cys  Glu  Ser  Gly  Ser  Phe  Thr  Ala  Ser  Glu  Asn  His  Leu  Arg  His
 1              5                        10                       15

Cys  Leu  Ser  Cys  Ser  Lys  Cys  Arg  Lys  Glu  Met  Gly  Gln  Val  Glu  Ile
              20                        25                       30

Ser  Ser  Cys  Thr  Val  Asp  Arg  Asp  Thr  Val  Cys
              35                        40
```

( 2 ) INFORMATION FOR SEQ ID NO: 32:

( i ) SEQUENCE CHARACTERISTICS:
  ( A ) LENGTH: 42 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO: 32:

```
Ser  Cys  Glu  Asp  Ser  Thr  Tyr  Thr  Gln  Leu  Trp  Asn  Trp  Val  Pro  Glu
 1              5                        10                       15

Cys  Leu  Ser  Cys  Gly  Ser  Arg  Cys  Ser  Ser  Asp  Gln  Val  Glu  Thr  Gln
              20                        25                       30

Ala  Cys  Thr  Arg  Glu  Gln  Asn  Arg  Ile  Cys
              35                        40
```

( 2 ) INFORMATION FOR SEQ ID NO: 33:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 33:

```
Pro  Cys  Leu  Asp  Asn  Val  Thr  Phe  Ser  Asp  Val  Val  Ser  Ala  Thr  Glu
 1              5                         10                        15

Pro  Cys  Lys  Pro  Cys  Thr  Glu  Cys  Leu  Gly  Leu  Gln  Ser  Met  Ser  Ala
              20                        25                        30

Pro  Cys  Val  Glu  Ala  Asp  Asp  Ala  Val  Cys
              35                        40
```

( 2 ) INFORMATION FOR SEQ ID NO: 34:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 34:

```
Pro  Cys  Gly  Glu  Ser  Glu  Phe  Leu  Asp  Thr  Trp  Asn  Arg  Glu  Thr  His
 1              5                         10                        15

Cys  His  Gln  His  Lys  Tyr  Cys  Asp  Pro  Asn  Leu  Gly  Leu  Arg  Val  Gln
              20                        25                        30

Gln  Lys  Gly  Thr  Ser  Glu  Thr  Asp  Thr  Ile  Cys
              35                        40
```

( 2 ) INFORMATION FOR SEQ ID NO: 35:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 35:

```
Pro  Cys  Glu  Pro  Gly  Phe  Tyr  Asn  Glu  Ala  Val  Asn  Tyr  Asp  Thr  Cys
 1              5                         10                        15

Lys  Gln  Cys  Thr  Gln  Cys  Asn  His  Arg  Ser  Gly  Ser  Glu  Leu  Lys  Gln
              20                        25                        30

Asn  Cys  Thr  Pro  Thr  Glu  Asp  Thr  Val  Cys
              35                        40
```

( 2 ) INFORMATION FOR SEQ ID NO: 36:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 36:

```
Gly  Cys  Arg  Lys  Asn  Gln  Tyr  Arg  His  Tyr  Trp  Ser  Glu  Asn  Leu  Phe
 1              5                         10                        15
```

Gln Cys Phe Asn Cys Ser Leu Cys Leu Asn Gly Thr Val His Leu Ser
            20                  25                  30

Cys Gln Glu Lys Gln Asn Thr Val Cys
            35                  40

(2) INFORMATION FOR SEQ ID NO: 37:

(i) SEQUENCE CHARACTERISTICS:
(A) LENGTH: 44 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 37:

Thr Cys Arg Pro Gly Trp Tyr Cys Ala Leu Ser Lys Gln Glu Gly Cys
1               5                   10                  15

Arg Leu Cys Ala Pro Leu Arg Lys Cys Arg Pro Gly Phe Gly Val Ala
            20                  25                  30

Arg Pro Gly Thr Glu Thr Ser Asp Val Val Cys Lys
            35                  40

(2) INFORMATION FOR SEQ ID NO: 38:

(i) SEQUENCE CHARACTERISTICS:
(A) LENGTH: 40 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 38:

Arg Cys Ala Tyr Gly Tyr Tyr Gln Asp Glu Glu Thr Gly His Cys Glu
1               5                   10                  15

Ala Cys Ser Val Cys Glu Val Gly Ser Gly Leu Val Phe Ser Cys Gln
            20                  25                  30

Asp Lys Gln Asn Thr Val Cys Glu
            35                  40

(2) INFORMATION FOR SEQ ID NO: 39:

(i) SEQUENCE CHARACTERISTICS:
(A) LENGTH: 41 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 39:

Thr Cys Glu Glu Gly Trp His Cys Thr Ser Glu Ala Cys Glu Ser Cys
1               5                   10                  15

Val Leu His Arg Ser Cys Ser Pro Gly Phe Gly Val Lys Gln Ile Ala
            20                  25                  30

Thr Gly Val Ser Asp Thr Ile Cys Glu
            35                  40

(2) INFORMATION FOR SEQ ID NO: 40:

(i) SEQUENCE CHARACTERISTICS:
(A) LENGTH: 39 amino acids
(B) TYPE: amino acid
(C) STRANDEDNESS: single (D) TOPOLOGY: linear (ii) MOLECULE TYPE: protein (xi) SEQUENCE DESCRIPTION: SEQ ID NO: 40:

```
Thr  Cys  His  Ala  Gly  Phe  Phe  Leu  Arg  Glu  Asn  Glu  Cys  Val  Ser  Cys
 1                   5                        10                       15

Ser  Asn  Cys  Lys  Lys  Ser  Leu  Glu  Cys  Thr  Lys  Leu  Cys  Leu  Pro  Gln
                20                        25                       30

Ile  Glu  Asn  Val  Lys  Gly  Thr
                35
```

(2) INFORMATION FOR SEQ ID NO: 41:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 41:

```
Pro  Cys  Ala  Pro  Gly  Thr  Phe  Ser  Asn  Thr  Thr  Ser  Ser  Thr  Asp  Ile
 1                   5                        10                       15

Cys  Arg  Pro  His  Gln  Ile  Cys  Asn  Val  Val  Ala  Ile  Pro  Gly  Asn  Ala
                20                        25                       30

Ser  Met  Asp  Ala  Val  Cys  Thr
                35
```

(2) INFORMATION FOR SEQ ID NO: 42:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 42:

```
Glu  Cys  Pro  Glu  Gly  Thr  Tyr  Ser  Asp  Glu  Ala  Asn  His  Val  Asp  Pro
 1                   5                        10                       15

Cys  Leu  Pro  Cys  Thr  Val  Cys  Glu  Asp  Thr  Glu  Arg  Gln  Leu  Arg  Glu
                20                        25                       30

Cys  Thr  Pro  Trp  Ala  Asp  Ala  Glu  Cys  Glu
                35                        40
```

(2) INFORMATION FOR SEQ ID NO: 43:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 43:

```
Pro  Cys  Pro  Val  Gly  Phe  Phe  Ser  Asn  Val  Ser  Ser  Ala  Phe  Glu  Lys
 1                   5                        10                       15

Cys  His  Pro  Trp  Thr  Ser  Cys  Glu  Thr  Lys  Asp  Leu  Val  Val  Gln  Gln
                20                        25                       30

Ala  Gly  Thr  Asn  Lys  Thr  Asp  Val  Val  Cys  Gly
                35                        40
```

( 2 ) INFORMATION FOR SEQ ID NO: 44:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 44:

```
Pro Cys Pro Pro Gly His Phe Ser Pro Gly Ser Asn Gln Ala Cys Lys
 1               5                  10                  15

Pro Trp Thr Asn Cys Thr Leu Ser Gly Lys Gln Ile Arg His Pro Ala
            20                  25                  30

Ser Asn Ser Leu Asp Thr Val Cys Glu
            35                  40
```

( 2 ) INFORMATION FOR SEQ ID NO: 45:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 45:

TGTCTGGCAT GG                                                                               1 2

( 2 ) INFORMATION FOR SEQ ID NO: 46:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 46:

CCCCAGATTT AG                                                                               1 2

( 2 ) INFORMATION FOR SEQ ID NO: 47:

( i ) SEQUENCE CHARACTERISTICS:
        ( A ) LENGTH: 600 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..597

( x i ) SEQUENCE DESCRIPTION: SEQ ID NO: 47:

```
ATG GGC CTC TCC ACC GTG CCT GAC CTG CTG CTG CCG CTG GTG CTC CTG      4 8
Met Gly Leu Ser Thr Val Pro Asp Leu Leu Leu Pro Leu Val Leu Leu
 1               5                  10                  15

GAG CTG TTG GTG GGA ATA TAC CCC TCA GGG GTT ATT GGA CTG GTC CCT      9 6
Glu Leu Leu Val Gly Ile Tyr Pro Ser Gly Val Ile Gly Leu Val Pro
            20                  25                  30

CAC CTA GGG GAC AGG GAG AAG AGA GAT AGT GTG TGT CCC ACA GGA AAA      1 4 4
His Leu Gly Asp Arg Glu Lys Arg Asp Ser Val Cys Pro Thr Gly Lys
```

|           |           |           |           |           |           |           |           |           |           |           |           |           |           |           |           |       |
|-----------|-----------|-----------|-----------|-----------|-----------|-----------|-----------|-----------|-----------|-----------|-----------|-----------|-----------|-----------|-----------|-------|
|           |           | 35        |           |           |           |           | 40        |           |           |           |           | 45        |           |           |           |       |
| TAT       | ATC       | CAC       | CCT       | CAA       | AAT       | AAT       | TCG       | ATT       | TGC       | TGT       | ACC       | AAG       | TGC       | CAC       | AAA       | 192   |
| Tyr       | Ile       | His       | Pro       | Gln       | Asn       | Asn       | Ser       | Ile       | Cys       | Cys       | Thr       | Lys       | Cys       | His       | Lys       |       |
|           |           | 50        |           |           |           | 55        |           |           |           |           | 60        |           |           |           |           |       |
| GGA       | ACC       | TAC       | TTG       | TAC       | AAT       | GAC       | TGT       | CCA       | GGC       | CCG       | GGG       | CAG       | GAT       | ACG       | GAC       | 240   |
| Gly       | Thr       | Tyr       | Leu       | Tyr       | Asn       | Asp       | Cys       | Pro       | Gly       | Pro       | Gly       | Gln       | Asp       | Thr       | Asp       |       |
| 65        |           |           |           |           | 70        |           |           |           |           | 75        |           |           |           |           | 80        |       |
| TGC       | AGG       | GAG       | TGT       | GAG       | AGC       | GGC       | TCC       | TTC       | ACC       | GCT       | TCA       | GAA       | AAC       | CAC       | CTC       | 288   |
| Cys       | Arg       | Glu       | Cys       | Glu       | Ser       | Gly       | Ser       | Phe       | Thr       | Ala       | Ser       | Glu       | Asn       | His       | Leu       |       |
|           |           |           |           | 85        |           |           |           |           | 90        |           |           |           |           | 95        |           |       |
| AGA       | CAC       | TGC       | CTC       | AGC       | TGC       | TCC       | AAA       | TGC       | CGA       | AAG       | GAA       | ATG       | GGT       | CAG       | GTG       | 336   |
| Arg       | His       | Cys       | Leu       | Ser       | Cys       | Ser       | Lys       | Cys       | Arg       | Lys       | Glu       | Met       | Gly       | Gln       | Val       |       |
|           |           |           | 100       |           |           |           |           | 105       |           |           |           |           | 110       |           |           |       |
| GAG       | ATC       | TCT       | TCT       | TGC       | ACA       | GTG       | GAC       | CGG       | GAC       | ACC       | GTG       | TGT       | GGC       | TGC       | AGG       | 384   |
| Glu       | Ile       | Ser       | Ser       | Cys       | Thr       | Val       | Asp       | Arg       | Asp       | Thr       | Val       | Cys       | Gly       | Cys       | Arg       |       |
|           |           | 115       |           |           |           |           | 120       |           |           |           |           | 125       |           |           |           |       |
| AAG       | AAC       | CAG       | TAC       | CGG       | CAT       | TAT       | TGG       | AGT       | GAA       | AAC       | CTT       | TTC       | CAG       | TGC       | TTC       | 432   |
| Lys       | Asn       | Gln       | Tyr       | Arg       | His       | Tyr       | Trp       | Ser       | Glu       | Asn       | Leu       | Phe       | Gln       | Cys       | Phe       |       |
|           | 130       |           |           |           |           | 135       |           |           |           |           | 140       |           |           |           |           |       |
| AAT       | TGC       | AGC       | CTC       | TGC       | CTC       | AAT       | GGG       | ACC       | GTG       | CAC       | CTC       | TCC       | TGC       | CAG       | GAG       | 480   |
| Asn       | Cys       | Ser       | Leu       | Cys       | Leu       | Asn       | Gly       | Thr       | Val       | His       | Leu       | Ser       | Cys       | Gln       | Glu       |       |
| 145       |           |           |           |           | 150       |           |           |           |           | 155       |           |           |           |           | 160       |       |
| AAA       | CAG       | AAC       | ACC       | GTG       | TGC       | ACC       | TGC       | CAT       | GCA       | GGT       | TTC       | TTT       | CTA       | AGA       | GAA       | 528   |
| Lys       | Gln       | Asn       | Thr       | Val       | Cys       | Thr       | Cys       | His       | Ala       | Gly       | Phe       | Phe       | Leu       | Arg       | Glu       |       |
|           |           |           |           | 165       |           |           |           |           | 170       |           |           |           |           | 175       |           |       |
| AAC       | GAG       | TGT       | GTC       | TCC       | TGT       | AGT       | AAC       | TGT       | AAG       | AAA       | AGC       | CTG       | GAG       | TGC       | ACG       | 576   |
| Asn       | Glu       | Cys       | Val       | Ser       | Cys       | Ser       | Asn       | Cys       | Lys       | Lys       | Ser       | Leu       | Glu       | Cys       | Thr       |       |
|           |           |           | 180       |           |           |           |           | 185       |           |           |           |           | 190       |           |           |       |
| AAG       | TTG       | TGC       | CTA       | CCC       | CAG       | ATT       | TAG       |           |           |           |           |           |           |           |           | 600   |
| Lys       | Leu       | Cys       | Leu       | Pro       | Gln       | Ile       |           |           |           |           |           |           |           |           |           |       |
|           |           | 195       |           |           |           | 200       |           |           |           |           |           |           |           |           |           |       |

( 2 ) INFORMATION FOR SEQ ID NO: 48:

( i ) SEQUENCE CHARACTERISTICS:
        ( A ) LENGTH: 199 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 48:

| Met | Gly | Leu | Ser | Thr | Val | Pro | Asp | Leu | Leu | Pro | Leu | Val | Leu | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Glu | Leu | Leu | Val | Gly | Ile | Tyr | Pro | Ser | Gly | Val | Ile | Gly | Leu | Val | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Leu | Gly | Asp | Arg | Glu | Lys | Arg | Asp | Ser | Val | Cys | Pro | Thr | Gly | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Ile | His | Pro | Gln | Asn | Asn | Ser | Ile | Cys | Cys | Thr | Lys | Cys | His | Lys |
|-----|-----|-----|-----|-----|-----|-----|-----|-----|-----|-----|-----|-----|-----|-----|-----|
|     |     | 50  |     |     |     | 55  |     |     |     |     | 60  |     |     |     |     |

| Gly | Thr | Tyr | Leu | Tyr | Asn | Asp | Cys | Pro | Gly | Pro | Gly | Gln | Asp | Thr | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Cys | Arg | Glu | Cys | Glu | Ser | Gly | Ser | Phe | Thr | Ala | Ser | Glu | Asn | His | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Arg | His | Cys | Leu | Ser | Cys | Ser | Lys | Cys | Arg | Lys | Glu | Met | Gly | Gln | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Glu | Ile | Ser | Ser | Cys | Thr | Val | Asp | Arg | Asp | Thr | Val | Cys | Gly | Cys | Arg |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Lys | Asn | Gln | Tyr | Arg | His | Tyr | Trp | Ser | Glu | Asn | Leu | Phe | Gln | Cys | Phe |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

```
Asn Cys Ser Leu Cys Leu Asn Gly Thr Val His Leu Ser Cys Gln Glu
145                 150                     155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Pro Gln Ile
            195
```

(2) INFORMATION FOR SEQ ID NO: 49:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..471

(xi) SEQUENCE DESCRIPTION: SEQ ID NO: 49:

```
ATG GGC CTC TCC ACC GTG CCT GAC CTG CTG CTG CCG CTG GTG CTC CTG    48
Met Gly Leu Ser Thr Val Pro Asp Leu Leu Leu Pro Leu Val Leu Leu
 1               5                  10                  15

GAG CTG TTG GTG GGA ATA TAC CCC TCA GGG GTT ATT GGA CTG GTC CCT    96
Glu Leu Leu Val Gly Ile Tyr Pro Ser Gly Val Ile Gly Leu Val Pro
                20                  25                  30

CAC CTA GGG GAC AGG GAG AAG AGA GAG TGT GAG AGC GGC TCC TTC ACC   144
His Leu Gly Asp Arg Glu Lys Arg Glu Cys Glu Ser Gly Ser Phe Thr
             35                  40                  45

GCT TCA GAA AAC CAC CTC AGA CAC TGC CTC AGC TGC TCC AAA TGC CGA   192
Ala Ser Glu Asn His Leu Arg His Cys Leu Ser Cys Ser Lys Cys Arg
         50                  55                  60

AAG GAA ATG GGT CAG GTG GAG ATC TCT TCT TGC ACA GTG GAC CGG GAC   240
Lys Glu Met Gly Gln Val Glu Ile Ser Ser Cys Thr Val Asp Arg Asp
 65                  70                  75                  80

ACC GTG TGT GGC TGC AGG AAG AAC CAG TAC CGG CAT TAT TGG AGT GAA   288
Thr Val Cys Gly Cys Arg Lys Asn Gln Tyr Arg His Tyr Trp Ser Glu
                 85                  90                  95

AAC CTT TTC CAG TGC TTC AAT TGC AGC CTC TGC CTC AAT GGG ACC GTG   336
Asn Leu Phe Gln Cys Phe Asn Cys Ser Leu Cys Leu Asn Gly Thr Val
                100                 105                 110

CAC CTC TCC TGC CAG GAG AAA CAG AAC ACC GTG TGC ACC TGC CAT GCA   384
His Leu Ser Cys Gln Glu Lys Gln Asn Thr Val Cys Thr Cys His Ala
            115                 120                 125

GGT TTC TTT CTA AGA GAA AAC GAG TGT GTC TCC TGT AGT AAC TGT AAG   432
Gly Phe Phe Leu Arg Glu Asn Glu Cys Val Ser Cys Ser Asn Cys Lys
130                 135                 140

AAA AGC CTG GAG TGC ACG AAG TTG TGC CTA CCC CAG ATT TAG            474
Lys Ser Leu Glu Cys Thr Lys Leu Cys Leu Pro Gln Ile
145                 150                 155
```

(2) INFORMATION FOR SEQ ID NO: 50:

(i) SEQUENCE CHARACTERISTICS:
        (A) LENGTH: 157 amino acids
        (B) TYPE: amino acid
        (D) TOPOLOGY: linear (ii) MOLECULE TYPE: protein ( x i ) SEQUENCE DESCRIPTION: SEQ ID NO: 50:

| Met | Gly | Leu | Ser | Thr | Val | Pro | Asp | Leu | Leu | Pro | Leu | Val | Leu | Leu |
|-----|-----|-----|-----|-----|-----|-----|-----|-----|-----|-----|-----|-----|-----|-----|
| 1   |     |     |     | 5   |     |     |     |     | 10  |     |     |     | 15  |     |

| Glu | Leu | Leu | Val | Gly | Ile | Tyr | Pro | Ser | Gly | Val | Ile | Gly | Leu | Val | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Leu | Gly | Asp | Arg | Glu | Lys | Arg | Glu | Cys | Glu | Ser | Gly | Ser | Phe | Thr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Ser | Glu | Asn | His | Leu | Arg | His | Cys | Leu | Ser | Cys | Ser | Lys | Cys | Arg |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Glu | Met | Gly | Gln | Val | Glu | Ile | Ser | Ser | Cys | Thr | Val | Asp | Arg | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Thr | Val | Cys | Gly | Cys | Arg | Lys | Asn | Gln | Tyr | Arg | His | Tyr | Trp | Ser | Glu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Leu | Phe | Gln | Cys | Phe | Asn | Cys | Ser | Leu | Cys | Leu | Asn | Gly | Thr | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| His | Leu | Ser | Cys | Gln | Glu | Lys | Gln | Asn | Thr | Val | Cys | Thr | Cys | His | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Gly | Phe | Phe | Leu | Arg | Glu | Asn | Glu | Cys | Val | Ser | Cys | Ser | Asn | Cys | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Lys | Ser | Leu | Glu | Cys | Thr | Lys | Leu | Cys | Leu | Pro | Gln | Ile |
|-----|-----|-----|-----|-----|-----|-----|-----|-----|-----|-----|-----|-----|
| 145 |     |     |     |     | 150 |     |     |     |     | 155 |     |     |

( 2 ) INFORMATION FOR SEQ ID NO: 51:

( i ) SEQUENCE CHARACTERISTICS:
        ( A ) LENGTH: 462 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..459

( x i ) SEQUENCE DESCRIPTION: SEQ ID NO: 51:

| ATG | GGC | CTC | TCC | ACC | GTG | CCT | GAC | CTG | CTG | CTG | CCG | CTG | GTG | CTC | CTG | 48 |
|-----|-----|-----|-----|-----|-----|-----|-----|-----|-----|-----|-----|-----|-----|-----|-----|----|
| Met | Gly | Leu | Ser | Thr | Val | Pro | Asp | Leu | Leu | Leu | Pro | Leu | Val | Leu | Leu |    |
| 1   |     |     |     | 5   |     |     |     |     | 10  |     |     |     |     | 15  |     |    |

| GAG | CTG | TTG | GTG | GGA | ATA | TAC | CCC | TCA | GGG | GTT | ATT | GGA | CTG | GTC | CCT | 96 |
|-----|-----|-----|-----|-----|-----|-----|-----|-----|-----|-----|-----|-----|-----|-----|-----|----|
| Glu | Leu | Leu | Val | Gly | Ile | Tyr | Pro | Ser | Gly | Val | Ile | Gly | Leu | Val | Pro |    |
|     |     |     | 20  |     |     |     |     | 25  |     |     |     |     | 30  |     |     |    |

| CAC | CTA | GGG | GAC | AGG | GAG | AAG | AGA | GAT | AGT | GTG | TGT | CCC | CAA | GGA | AAA | 144 |
|-----|-----|-----|-----|-----|-----|-----|-----|-----|-----|-----|-----|-----|-----|-----|-----|-----|
| His | Leu | Gly | Asp | Arg | Glu | Lys | Arg | Asp | Ser | Val | Cys | Pro | Gln | Gly | Lys |     |
|     |     | 35  |     |     |     |     | 40  |     |     |     |     | 45  |     |     |     |     |

| TAT | ATC | CAC | CCT | CAA | AAT | AAT | TCG | ATT | TGC | TGT | ACC | AAG | TGC | CAC | AAA | 192 |
|-----|-----|-----|-----|-----|-----|-----|-----|-----|-----|-----|-----|-----|-----|-----|-----|-----|
| Tyr | Ile | His | Pro | Gln | Asn | Asn | Ser | Ile | Cys | Cys | Thr | Lys | Cys | His | Lys |     |
|     * 50 |     |     |     |     | 55  |     |     |     |     | 60  |     |     |     |     |     |

| GGA | ACC | TAC | TTG | TAC | AAT | GAC | TGT | CCA | GGC | CCG | GGG | CAG | GAT | ACG | GAC | 240 |
|-----|-----|-----|-----|-----|-----|-----|-----|-----|-----|-----|-----|-----|-----|-----|-----|-----|
| Gly | Thr | Tyr | Leu | Tyr | Asn | Asp | Cys | Pro | Gly | Pro | Gly | Gln | Asp | Thr | Asp |     |
| 65  |     |     |     |     | 70  |     |     |     |     | 75  |     |     |     |     | 80  |     |

| TGC | AGG | AAG | AAC | CAG | TAC | CGG | CAT | TAT | TGG | AGT | GAA | AAC | CTT | TTC | CAG | 288 |
|-----|-----|-----|-----|-----|-----|-----|-----|-----|-----|-----|-----|-----|-----|-----|-----|-----|
| Cys | Arg | Lys | Asn | Gln | Tyr | Arg | His | Tyr | Trp | Ser | Glu | Asn | Leu | Phe | Gln |     |
|     |     |     |     | 85  |     |     |     |     | 90  |     |     |     |     | 95  |     |     |

| TGC | TTC | AAT | TGC | AGC | CTC | TGC | CTC | AAT | GGG | ACC | GTG | CAC | CTC | TCC | TGC | 336 |
|-----|-----|-----|-----|-----|-----|-----|-----|-----|-----|-----|-----|-----|-----|-----|-----|-----|
| Cys | Phe | Asn | Cys | Ser | Leu | Cys | Leu | Asn | Gly | Thr | Val | His | Leu | Ser | Cys |     |
|     |     |     | 100 |     |     |     |     | 105 |     |     |     |     | 110 |     |     |     |

| CAG | GAG | AAA | CAG | AAC | ACC | GTG | TGC | ACC | TGC | CAT | GCA | GGT | TTC | TTT | CTA | 384 |
|-----|-----|-----|-----|-----|-----|-----|-----|-----|-----|-----|-----|-----|-----|-----|-----|-----|
| Gln | Glu | Lys | Gln | Asn | Thr | Val | Cys | Thr | Cys | His | Ala | Gly | Phe | Phe | Leu |     |
|     |     | 115 |     |     |     |     | 120 |     |     |     |     | 125 |     |     |     |     |

```
AGA GAA AAC GAG TGT GTC TCC TGT AGT AAC TGT AAG AAA AGC CTG GAG      432
Arg Glu Asn Glu Cys Val Ser Cys Ser Asn Cys Lys Lys Ser Leu Glu
    130                 135                 140

TGC ACG AAG TTG TGC CTA CCC CAG ATT TAG                              462
Cys Thr Lys Leu Cys Leu Pro Gln Ile
145                 150
```

( 2 ) INFORMATION FOR SEQ ID NO: 52:

( i ) SEQUENCE CHARACTERISTICS:
        ( A ) LENGTH: 153 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 52:

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Lys Asn Gln Tyr Arg His Tyr Trp Ser Glu Asn Leu Phe Gln
                85                  90                  95

Cys Phe Asn Cys Ser Leu Cys Leu Asn Gly Thr Val His Leu Ser Cys
                100                 105                 110

Gln Glu Lys Gln Asn Thr Val Cys Thr Cys His Ala Gly Phe Phe Leu
            115                 120                 125

Arg Glu Asn Glu Cys Val Ser Cys Ser Asn Cys Lys Lys Ser Leu Glu
    130                 135                 140

Cys Thr Lys Leu Cys Leu Pro Gln Ile
145                 150
```

( 2 ) INFORMATION FOR SEQ ID NO: 53:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..474

( x i ) SEQUENCE DESCRIPTION: SEQ ID NO: 53:

```
ATG GGC CTC TCC ACC GTG CCT GAC CTG CTG CTG CCG CTG GTG CTC CTG      48
Met Gly Leu Ser Thr Val Pro Asp Leu Leu Leu Pro Leu Val Leu Leu
1               5                   10                  15

GAG CTG TTG GTG GGA ATA TAC CCC TCA GGG GTT ATT GGA CTG GTC CCT      96
Glu Leu Leu Val Gly Ile Tyr Pro Ser Gly Val Ile Gly Leu Val Pro
            20                  25                  30

CAC CTA GGG GAC AGG GAG AAG AGA GAT AGT GTG TGT CCC CAA GGA AAA     144
His Leu Gly Asp Arg Glu Lys Arg Asp Ser Val Cys Pro Gln Gly Lys
        35                  40                  45
```

```
TAT ATC CAC CCT CAA AAT AAT TCG ATT TGC TGT ACC AAG TGC CAC AAA      192
Tyr Ile His Pro Gln Asn Asn Ser Ile Cys Cys Thr Lys Cys His Lys
    50                  55                  60

GGA ACC TAC TTG TAC AAT GAC TGT CCA GGC CCG GGG CAG GAT ACG GAC      240
Gly Thr Tyr Leu Tyr Asn Asp Cys Pro Gly Pro Gly Gln Asp Thr Asp
65                  70                  75                  80

TGC AGG GAG TGT GAG AGC GGC TCC TTC ACC GCT TCA GAA AAC CAC CTC      288
Cys Arg Glu Cys Glu Ser Gly Ser Phe Thr Ala Ser Glu Asn His Leu
                85                  90                  95

AGA CAC TGC CTC AGC TGC TCC AAA TGC CGA AAG GAA ATG GGT CAG GTG      336
Arg His Cys Leu Ser Cys Ser Lys Cys Arg Lys Glu Met Gly Gln Val
            100                 105                 110

GAG ATC TCT TCT TGC ACA GTG GAC CGG GAC ACC GTG TGT ACC TGC CAT      384
Glu Ile Ser Ser Cys Thr Val Asp Arg Asp Thr Val Cys Thr Cys His
        115                 120                 125

GCA GGT TTC TTT CTA AGA GAA AAC GAG TGT GTC TCC TGT AGT AAC TGT      432
Ala Gly Phe Phe Leu Arg Glu Asn Glu Cys Val Ser Cys Ser Asn Cys
    130                 135                 140

AAG AAA AGC CTG GAG TGC ACG AAG TTG TGC CTA CCC CAG ATT TAG          477
Lys Lys Ser Leu Glu Cys Thr Lys Leu Cys Leu Pro Gln Ile
145                 150                 155
```

( 2 ) INFORMATION FOR SEQ ID NO: 54:

( i ) SEQUENCE CHARACTERISTICS:
        ( A ) LENGTH: 158 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 54:

```
Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Thr Cys His
        115                 120                 125

Ala Gly Phe Phe Leu Arg Glu Asn Glu Cys Val Ser Cys Ser Asn Cys
    130                 135                 140

Lys Lys Ser Leu Glu Cys Thr Lys Leu Cys Leu Pro Gln Ile
145                 150                 155
```

( 2 ) INFORMATION FOR SEQ ID NO: 55:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO: 55:

GTGTGCACCT GA 12

( 2 ) INFORMATION FOR SEQ ID NO: 56:

( i ) SEQUENCE CHARACTERISTICS:
        ( A ) LENGTH: 504 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: CDS
        ( B ) LOCATION: 1..501

( x i ) SEQUENCE DESCRIPTION: SEQ ID NO: 56:

```
ATG  GGC  CTC  TCC  ACC  GTG  CCT  GAC  CTG  CTG  CTG  CCG  CTG  GTG  CTC  CTG      48
Met  Gly  Leu  Ser  Thr  Val  Pro  Asp  Leu  Leu  Leu  Pro  Leu  Val  Leu  Leu
 1              5                        10                       15

GAG  CTG  TTG  GTG  GGA  ATA  TAC  CCC  TCA  GGG  GTT  ATT  GGA  CTG  GTC  CCT      96
Glu  Leu  Leu  Val  Gly  Ile  Tyr  Pro  Ser  Gly  Val  Ile  Gly  Leu  Val  Pro
                20                       25                       30

CAC  CTA  GGG  GAC  AGG  GAG  AAG  AGA  GAT  AGT  GTG  TGT  CCC  CAA  GGA  AAA     144
His  Leu  Gly  Asp  Arg  Glu  Lys  Arg  Asp  Ser  Val  Cys  Pro  Gln  Gly  Lys
           35                       40                       45

TAT  ATC  CAC  CCT  CAA  AAT  AAT  TCG  ATT  TGC  TGT  ACC  AAG  TGC  CAC  AAA     192
Tyr  Ile  His  Pro  Gln  Asn  Asn  Ser  Ile  Cys  Cys  Thr  Lys  Cys  His  Lys
      50                       55                       60

GGA  ACC  TAC  TTG  TAC  AAT  GAC  TGT  CCA  GGC  CCG  GGG  CAG  GAT  ACG  GAC     240
Gly  Thr  Tyr  Leu  Tyr  Asn  Asp  Cys  Pro  Gly  Pro  Gly  Gln  Asp  Thr  Asp
 65                       70                       75                       80

TGC  AGG  GAG  TGT  GAG  AGC  GGC  TCC  TTC  ACC  GCT  TCA  GAA  AAC  CAC  CTC     288
Cys  Arg  Glu  Cys  Glu  Ser  Gly  Ser  Phe  Thr  Ala  Ser  Glu  Asn  His  Leu
                85                       90                       95

AGA  CAC  TGC  CTC  AGC  TGC  TCC  AAA  TGC  CGA  AAG  GAA  ATG  GGT  CAG  GTG     336
Arg  His  Cys  Leu  Ser  Cys  Ser  Lys  Cys  Arg  Lys  Glu  Met  Gly  Gln  Val
               100                      105                      110

GAG  ATC  TCT  TCT  TGC  ACA  GTG  GAC  CGG  GAC  ACC  GTG  TGT  GGC  TGC  AGG     384
Glu  Ile  Ser  Ser  Cys  Thr  Val  Asp  Arg  Asp  Thr  Val  Cys  Gly  Cys  Arg
          115                      120                      125

AAG  AAC  CAG  TAC  CGG  CAT  TAT  TGG  AGT  GAA  AAC  CTT  TTC  CAG  TGC  TTC     432
Lys  Asn  Gln  Tyr  Arg  His  Tyr  Trp  Ser  Glu  Asn  Leu  Phe  Gln  Cys  Phe
     130                      135                      140

AAT  TGC  AGC  CTC  TGC  CTC  AAT  GGG  ACC  GTG  CAC  CTC  TCC  TGC  CAG  GAG     480
Asn  Cys  Ser  Leu  Cys  Leu  Asn  Gly  Thr  Val  His  Leu  Ser  Cys  Gln  Glu
145                      150                      155                      160

AAA  CAG  AAC  ACC  GTG  TGC  ACC  TGA                                              504
Lys  Gln  Asn  Thr  Val  Cys  Thr
                     165
```

( 2 ) INFORMATION FOR SEQ ID NO: 57:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 57:

```
Met  Gly  Leu  Ser  Thr  Val  Pro  Asp  Leu  Leu  Leu  Pro  Leu  Val  Leu  Leu
 1              5                        10                       15
```

-continued

| | | | | | | | | | | | | | | | |
|---|---|---|---|---|---|---|---|---|---|---|---|---|---|---|---|
| Glu | Leu | Leu | Val<br>20 | Gly | Ile | Tyr | Pro | Ser<br>25 | Gly | Val | Ile | Gly | Leu<br>30 | Val | Pro |
| His | Leu | Gly<br>35 | Asp | Arg | Glu | Lys | Arg<br>40 | Asp | Ser | Val | Cys | Pro<br>45 | Gln | Gly | Lys |
| Tyr | Ile<br>50 | His | Pro | Gln | Asn | Asn<br>55 | Ser | Ile | Cys | Cys | Thr<br>60 | Lys | Cys | His | Lys |
| Gly<br>65 | Thr | Tyr | Leu | Tyr | Asn<br>70 | Asp | Cys | Pro | Gly | Pro<br>75 | Gly | Gln | Asp | Thr | Asp<br>80 |
| Cys | Arg | Glu | Cys | Glu<br>85 | Ser | Gly | Ser | Phe | Thr<br>90 | Ala | Ser | Glu | Asn | His<br>95 | Leu |
| Arg | His | Cys | Leu<br>100 | Ser | Cys | Ser | Lys | Cys<br>105 | Arg | Lys | Glu | Met | Gly<br>110 | Gln | Val |
| Glu | Ile | Ser<br>115 | Ser | Cys | Thr | Val | Asp<br>120 | Arg | Asp | Thr | Val | Cys<br>125 | Gly | Cys | Arg |
| Lys | Asn<br>130 | Gln | Tyr | Arg | His | Tyr<br>135 | Trp | Ser | Glu | Asn | Leu<br>140 | Phe | Gln | Cys | Phe |
| Asn<br>145 | Cys | Ser | Leu | Cys | Leu<br>150 | Asn | Gly | Thr | Val | His<br>155 | Leu | Ser | Cys | Gln | Glu<br>160 |
| Lys | Gln | Asn | Thr | Val<br>165 | Cys | Thr | | | | | | | | | |

We claim:

1. A polypeptide which is capable of binding human TNFα and which has the first three cysteine-rich subdomains, but not the fourth cysteine-rich subdomain, of the extracellular binding domain of a receptor selected from the group consisting of the 55 kD and 75 kD receptors for human TNFα.

2. A polypeptide according to claim 1, which has the amino acid sequence of SEQ ID NO: 2.

3. A polypeptide according to claim 1, which has the amino acid sequence of SEQ ID NO: 4.

4. A process for the preparation of a polypeptide which is capable of binding human TNFα and which has the first three cysteine-rich subdomains but not the fourth cysteine-rich subdomain of the extracellular binding domain of a receptor selected from the group consisting of the 55 kD and 75 kD receptors for human TNFα, which process comprises (i) culturing a host transformed with a vector encoding said polypeptide under such conditions that said polypeptide is expressed; and (ii) isolating said polypeptide.

5. A process according to claim 4, wherein said polypeptide has the amino acid sequence of SEQ ID NO: 2.

6. A process according to claim 4, wherein said polypeptide has the amino acid sequence of SEQ ID NO: 4.

7. A pharmaceutical composition comprising a pharmaceutically acceptable carrier or diluent and, as an active principle, a polypeptide which is capable of binding human TNFα and which has the first three cysteine-rich subdomains, but not the fourth cysteine-rich subdomain, of the extracellular binding domain of a receptor selected from the group consisting of the 55 kD and 75 kD receptors for human TNFα.

8. A composition according to claim 7, wherein said polypeptide has the amino acid sequence of SEQ ID NO: 2.

9. A composition according to claim 7, wherein said polypeptide has the amino acid sequence of SEQ ID NO: 4.

* * * * *